US005707985A

United States Patent [19]

McKenzie et al.

[11] Patent Number: 5,707,985
[45] Date of Patent: Jan. 13, 1998

[54] NAPHTHYL-, QUINOLYL- AND ISOQUINOLYL- SULFONAMIDE DERIVATIVES AS CELL ADHESION MODULATORS

[75] Inventors: Thomas Charles McKenzie, Carlsbad; Gilbert M. Rishton, Del Mar, both of Calif.; Nancy K. Harn, Indianapolis, Ind.; Wolfgang Scholz; James Hu, both of San Diego, Calif.

[73] Assignee: Tanabe Seiyaku Co. Ltd., Osaka, Japan

[21] Appl. No.: 472,645

[22] Filed: Jun. 7, 1995

[51] Int. Cl.$^6$ ............ A61K 31/395; A61K 31/55; C07D 471/02

[52] U.S. Cl. ............ 514/183; 514/213; 514/307; 514/314; 514/311; 514/305; 540/477; 540/582; 540/584; 540/546; 540/552; 546/139; 546/172

[58] Field of Search ............ 540/477, 582, 540/584, 546, 552; 546/139, 172; 514/183, 214, 307, 314, 311, 305

[56] References Cited

U.S. PATENT DOCUMENTS

| | | | |
|---|---|---|---|
| 3,239,506 | 3/1966 | Stanin et al. | 260/239 |
| 3,294,640 | 12/1966 | Wolf | 167/65 |
| 3,856,840 | 12/1974 | O'Brien et al. | 260/429.7 |
| 4,069,254 | 1/1978 | Hidaka et al. | 260/356 R |
| 4,288,595 | 9/1981 | Ledig et al. | 544/250 |
| 4,565,877 | 1/1986 | Wada et al. | 548/530 |
| 4,743,611 | 5/1988 | Malamas et al. | 514/390 |
| 4,829,079 | 5/1989 | Toja et al. | 514/425 |
| 4,885,306 | 12/1989 | Toja et al. | 514/425 |
| 4,952,235 | 8/1990 | Andree et al. | 71/94 |
| 4,990,523 | 2/1991 | Nolan et al. | 514/363 |
| 4,990,531 | 2/1991 | Galliani et al. | 548/425 |
| 5,037,822 | 8/1991 | Toja et al. | 514/212 |
| 5,041,436 | 8/1991 | Toja et al. | 514/212 |
| 5,164,514 | 11/1992 | Galliani et al. | 548/542 |
| 5,214,204 | 5/1993 | Dellaria et al. | 562/623 |
| 5,338,755 | 8/1994 | Wagnon et al. | 514/414 |
| 5,344,849 | 9/1994 | Bartroli et al. | 514/374 |
| 5,360,813 | 11/1994 | Bartroli et al. | 514/383 |
| 5,397,801 | 3/1995 | Wagnon et al. | 514/418 |

FOREIGN PATENT DOCUMENTS

| | | | |
|---|---|---|---|
| 0471841 | 2/1992 | European Pat. Off. | 514/311 |
| 50-131942 | 10/1975 | Japan | A61K 31/18 |
| 51-105080 | 9/1976 | Japan | C07D 239/54 |
| 52-100439 | 8/1977 | Japan | A61K 31/18 |
| 56-68610 | 6/1981 | Japan | A61K 31/18 |
| 62-201873 | 9/1987 | Japan | C07D 233/80 |
| 63-17870 | 1/1988 | Japan | C07D 243/08 |
| 63-215624 | 9/1988 | Japan | A61R 31/40 |
| 6419063 | 1/1989 | Japan | C07D 207/08 |
| 029863 | 1/1990 | Japan | C07D 217/26 |
| 2273610 | 11/1990 | Japan | A61K 7/06 |
| 4198161 | 7/1992 | Japan | C07C 311/41 |
| 9208464 | 5/1992 | WIPO | 514/311 |
| 9221313 | 10/1992 | WIPO | |
| 9305014 | 3/1993 | WIPO | A61K 31/18 |
| 9313072 | 7/1993 | WIPO | A61K 3/47 |
| 9401412 | 1/1994 | WIPO | C07D 237/09 |
| 9407496 | 4/1994 | WIPO | A61K 31/445 |

OTHER PUBLICATIONS

Chemical Abstracts, vol. 115, No. 220578c (1991).
Chemical Abstracts, vol. 59, No. 6393c (?) (1963).
J. Heterocyclic Chem. 18, 1–7 (1981).
Chemical Abstracts, vol. 91, No. 211132m (1979).
Tetrahedron Letters No. 7, pp. 635–638 (1977).
J. Chem. Eng. Data, vol. 15, No. 2, pp. 351–352 (1970).
J. Biol. Chem. vol. 269, No. 47, pp. 29389–29394 (1994).
Biochim. Biophys. Acta, vol. 1143, pp. 38–44 (1993).
Cancer Research, vol. 50, pp. 5399–5405 (1990).
Chemical Abstract, vol. 98, No. 209587q (1983).
Chemical Abstract, vol. 95, No. 93049x (1981).
Biochemistry, vol. 18, No. 9, pp. 1756–1765 (1979).
Chemical Abstracts, vol. 90, No. 163624d (1979).
Chemical Abstracts, vol. 80, No. 91081t (1974).
Chemical Abstracts, vol. 76, No. 41826m (1972).

*Primary Examiner*—Robert T. Bond
*Attorney, Agent, or Firm*—Birch, Stewart, Kolasch & Birch, LLP

[57] ABSTRACT

There are disclosed novel substituted naphthyl-, quinolyl- and isoquinolyl- sulfonamide derivatives that are useful in a method of treating immuno-inflammatory diseases in a mammalian patient suffering therefrom. Pharmaceutical compositions containing the sulfonamide compounds are also provided.

27 Claims, No Drawings

NAPHTHYL-, QUINOLYL- AND ISOQUINOLYL- SULFONAMIDE DERIVATIVES AS CELL ADHESION MODULATORS

FIELD OF THE INVENTION

The present invention describes the discovery of substituted naphthyl-, quinolyl- and isoquinolyl- sulfonamide derivatives which inhibit LFA-1-mediated cell adhesion and aggregation of lymphocytes. The compounds are useful in treating specific and non-specific inflammation, ischemia reperfusion, transplant rejection and asthma. Pharmaceutical compositions containing the sulfonamide compounds are also provided.

BACKGROUND OF THE INVENTION

Vascular endothelial cells form the interface between blood and tissues and control the passage of leukocytes as well as plasma fluid into tissues. A variety of signals generated at the site of inflammation can activate both endothelial cells as well as circulating leukocytes so that they become more adhesive to one another. Activation of endothelium and leukocytes initiates a complex adhesion cascade. This adhesion cascade involves the "tethering" of the leukocytes to the endothelium, after which they "roll" along the endothelial surface and finally strongly adhere and migrate into tissue to perform host defense functions. Several adhesion molecules, belonging to a super gene family consisting of non-covalently associated heterodimeric proteins called integrins, have been identified as being involved in leukocyte-endothelial cell interactions.

The $\beta_2$ integrin subfamily includes LFA-1 (CD11a/CD18), Mac-1 (CD11b/CD18, CR3) and p150/95 (CD11c/CD18, CR4). The known ligands for LFA-1 are ICAM-1, ICAM-2 and ICAM-3. The Intracellular Adhesion Molecules (ICAM) are also members of the Ig gene superfamily. ICAM-1 is the most ubiquitous of the ICAMs, being expressed in low levels on most peripheral blood leukocytes as well as endothelial cells, fibroblasts and dendritic cells. Cytokine activation of endothelial cells induces a dramatic increase in the expression of ICAM-1 and LFA-1/ICAM-1 interactions which are integral to both lymphocyte adhesion and transmigration through the endothelial barrier; Dustin, M. L. et al., *J. Immunol.*, 137, 245–254 (1986). ICAM-2 is primarily constitutively expressed on endothelial cells; de Fougerolles, A. R. et al., *J. Exp. Med.*, 174, 253–267 (1991), and ICAM-3 is largely found on resting lymphocytes, monocytes and neutrophils; and shows increased expression upon T cell activation; de Fougerolles, A. R. and Springer, T. A., *J. Exp. Med.*, 175, 185–190 (1992).

In addition to its critical role in the mediating of cellular adhesion, ICAM-1 has also been shown to act as a receptor for a subgroup of rhinoviruses and soluble ICAM-1 has been shown to act as specific inhibitor of rhinovirus infection; Martin, S. D. et al., *Nature*, 344, 70–72 (1990). A compound which blocks the interaction of rhinovirus with ICAM-1 may be a powerful pharmacological agent for the prevention and treatment of colds and secondary complications arising from rhinovirus infection.

Support for the importance of $\beta_2$ integrins in mediating inflammatory responses has been demonstrated by the ability of monoclonal antibodies which recognize LFA-1 to block CTL-mediated lysis of target cells, as well as inhibiting proliferation of T cells in response to soluble antigens, alloantigens and mitogen. Pathologies relating to a deficiency of $\beta_2$ integrin expression include clinical abnormalities including delayed separation of the umbilical stump and patent urachus, poor wound healing and the absence of pus formation, recurrent bacterial and fungal infections, focal or spreading skin and subcutaneous infections, otitis, mucositis, gingivitis, periodontitis, and neutrophilia in the absence of infection (Anderson and Springer, Ann. Rev. Med. 38:175 (1987); Springer et al., J. Exp. Med. 160:1901 (1984)).

Several in vivo models have demonstrated the importance of $\beta_2$ integrins in delayed-type hypersensitivity. α-LFA-1 antibodies have been shown to block the migration of spleen T cells to sites of dermal inflammation as well as the homing of lymph node and spleen T cells to peripheral and mesenteric lymph node in rats; Issekutz, T. B., *J. Immunol.*, 149, 3394–3402 (1992). Both α-LFA-1 and α-ICAM-1 antibodies can reduce ear swelling caused by edema and cell infiltration in association with delayed-type hypersensitivity; Scheynius, A. et al., *J. immunol.*, 150, 655–663 (1993).

The role of $\beta_2$ integrins in allograft rejection has been demonstrated by the ability of α-ICAM-1 antibodies to control allograft rejection and reperfusion injury in humans; Cosimi, A. B. et al., *J. Immunol.*, 144, 4604–4612 (1990); Haug et al., *Transplantation*, 55, 766–773 (1993).

Anti-ICAM-1 antibodies have also been shown to attenuate airway eosinophilia, hyper-responsiveness and asthma symptoms in a primate asthma model.

SUMMARY OF THE INVENTION

A primary objective of the present invention is to provide advantageous compounds which are effective in a broad method of treating immuno-inflammatory diseases in a mammalian patient, particularly in a human patient suffering from such a disease.

Another objective of the present invention is to provide an advantageous method of treating immuno-inflammatory diseases in a mammalian patient, particularly in a human, wherein the immuno-inflammatory disease is selected from the group consisting of specific and non-specific inflammation, transplant rejection, allograft rejection, ischemia reprofusion, asthma/allergy, delayed type hypersensitivity, contact hypersensitivity, rheumatoid arthritis, rhino virus and human immunodeficiency virus (HIV).

In accordance with these objectives, the present invention provides novel compounds which are useful in therapeutic methods of treating immuno-inflammatory diseases in a mammalian patient, especially humans. These novel compounds are encompassed by the following formula (I).

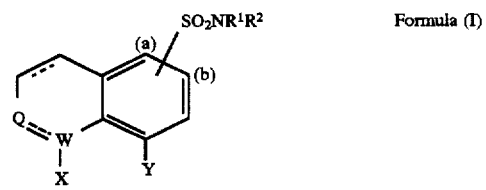

Formula (I)

wherein,
- W and Q are selected from a carbon and a nitrogen atom, provided that W and Q are not both simultaneously nitrogen atoms,
- X and Y may be the same or different and are selected from a hydrogen atom, a halogen atom, —$OR^3$, $NH_2$, —$NHR^4$ and —$NR^5R^6$,
- (a) and (b) denote ring positions which may be substituted with the sulfonyl moiety (—$SO_2$—), dotted lines denote optional double bonds, R¹ and R² may be the same or different and are selected from a hydrogen atom, $C_{1-8}$ alkyl, $C_{2-8}$ alkenyl, amino alkyl, $C_{3-9}$ cycloalkyl, aryl, heteroaryl, aryl substituted $C_{1-8}$ alkyl, heteroaryl substituted $C_{1-8}$ alkyl, haloaryl substituted $C_{1-8}$ alkyl, 1-adamantyl, 2-adamantyl, bornyl, 1-adamantanemethyl, 3-noradamantyl, 3-aminoquinuclidine, 3-adamantane-carboxylic acid-1-yl, 2-oxaadamantane-1-yl, 1-azaadamantane-4-yl and 1-hydroxy-3-adamantyl, 1-hydroxy-2-azahomoadamantane-6-yl, or alternatively R¹ and R² together with the nitrogen atom to which they are attached form either (1) a substituted or unsubstituted monocyclic moiety containing from 2 to 30 carbon atoms, or (2) a substituted or unsubstituted bridged polycyclic moiety containing from 6 to 30 carbon atoms, R³ to R⁶ may be the same or different and are selected from a hydrogen atom, $C_{1-8}$ alkyl, $C_{3-9}$ cycloalkyl, aryl, heteroaryl, aryl substituted $C_{1-8}$ alkyl, heteroaryl substituted $C_{1-8}$ alkyl, haloaryl substituted $C_{1-8}$ alkyl, alkoxy, arylalkanoylcarbonyl, aryl substituted $C_{2-8}$ alkanoyl, heteroaryl substituted $C_{2-8}$ alkanoyl and haloaryl substituted $C_{2-8}$ alkanoyl, and the pharmaceutically acceptable salts thereof.

The compound 3-(2-naphthylsulfonyl)-3-azabicyclo [3.2.2]nonane is excluded from the above described novel formula (I) compounds by proviso; however, this compound is encompassed by and useful in the advantageous methods of treatment and pharmaceutical compositions that are disclosed below.

In accordance with the objectives of the present invention, there are also provided novel pharmaceutical compositions that are useful in a method of treating an immuno-inflammatory disease in a patient suffering from such a disease. The pharmaceutical compositions provided contain a pharmaceutically effective amount of one or more of the formula (I) compounds of the present invention in combination with a pharmaceutically acceptable carrier or diluent therefor, for treating an encountered immuno-inflammatory disease in a mammalian patient suffering therefrom.

In accordance with the objectives of the present invention, there is also provided an advantageous method of treating immuno-inflammatory diseases in a patient suffering therefrom. The method entails administering a pharmaceutically effective amount of a formula (I) compound to the patient, preferably in the form of a pharmaceutical composition as provided for herein. Exemplary of such diseases are specific and non-specific inflammation, transplant rejection, allograft rejection, ischemia reprofusion, asthma/allergy, delayed type hypersensitivity, contact hypersensitivity, rheumatoid arthritis, rhino virus, and human immunodeficiency virus (HIV).

In formula (I), when R¹ and R² together with the nitrogen atom to which they are attached form a monocyclic moiety—it is preferably a substituted or unsubstituted monocyclic moiety of the following formula

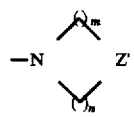

wherein Z' is selected from the group consisting of —$CH_2$— and —CHR'—, m and n are each an integer of 0 to 5, provided that m+n is >0, and R' is selected from the group consisting of $C_{1-8}$ alkyl, $C_{2-8}$ alkenyl, $C_{3-9}$ cycloalkyl, aryl, arylalkoxy, heteroaryl, aryl substituted $C_{1-8}$ alkyl, heteroaryl substituted $C_{1-8}$ alkyl, haloaryl substituted $C_{1-8}$ alkyl and 1-adamantyl.

In formula (I), when R¹ and R² combine with the adjacent nitrogen atom to form a bridged polycyclic moiety—it is preferably a substituted or unsubstituted bridged bicyclo moiety which is represented by the following formula

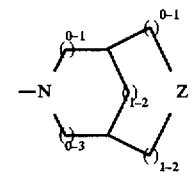

wherein, Z is selected from the group consisting of —$CH_2$—, —O—, —S—, —$SO_2$—, $N(R^7)$— and —$N[C(O)R^8]$—, wherein R⁷ and R⁸ may be the same or different and are selected from a hydrogen atom, $C_{1-8}$ alkyl, $C_{3-9}$ cycloalkyl, aryl, heteroaryl, aryl substituted $C_{1-8}$ alkyl, heteroaryl substituted $C_{1-8}$ alkyl, haloaryl substituted $C_{1-8}$ alkyl and 1-adamantyl.

More preferably, when R¹ and R₂ together with the nitrogen atom to which they are attached form a substituted or unsubstituted bridged bicyclo moiety having 6 to 30 carbon atoms, they form a substituted or unsubstituted bicyclo moiety selected from the group consisting of 3-azabicyclo[3.3.2]decane, 3-azabicyclo-[3.2.2]nonane, 3-azabicyclo[3.2.11]octane, 4-azahomo adamantane, 2-azaadamantane, 2-thia-5-azabicyclo[2.2.1]-heptane, 2-oxo-5-azabicyclo[2.2.1]heptane, 2,5-diaza bicyclo[2.2.1] heptane, 5-methylformyl-2,5-diazabicyclo-[2.2.1]heptane and 1-hydroxy-4-azahomoadamantyl-2-yl.

Preferred compounds of formula (I) for use in the treatment methods of the present invention include the following, but are not limited thereto:

(a) compounds wherein Q is a carbon atom and W is a nitrogen atom, (b) compounds wherein Q is a nitrogen atom and W is a carbon atom, (c) compounds wherein Q and W are each carbon atoms, (d) compounds wherein Q and W are each carbon atoms, X is a chlorine atom, Y is a hydrogen atom, R¹ is an adamantyl group and R² is a hydrogen atom, (e) compounds wherein Q and W are each carbon atoms, X is a chlorine atom, Y is a hydrogen atom, and R¹ and R² and the nitrogen atom to which they are mutually bonded form a bridged bicyclo moiety selected from the group consisting of 4-azahomoadamantane and 3-azabicyclo[3.2.2]nonane, (f) compounds wherein Q and W are each carbon atoms, X is a hydrogen atom, Y is an 3-pyridinylmethoxy group, and R¹ and R² and the nitrogen atom to which they are mutually bonded form a bridged bicyclo moiety selected from the group consisting of 4-azahamo adamantane and 3-azabicyclo[3.2.2] nonane, and (g) 5-Chloro-2-naphthalenesulfonamides encompassed by formula (I).

DETAILED DESCRIPTION OF THE INVENTION

The following detailed description is provided as an aid to those desiring to practice the present invention. The present invention, however, is not limited by this description or the Examples provided herein, since those of ordinary skill in the art will readily realize that various changes can be made in the materials and procedures set forth herein without departing from the spirit or scope of the present inventive discovery.

To better facilitate a thorough understanding of the present inventive discovery, this Detailed Description of the Invention is divided into the following parts.

Part I—Glossary of Terms and Abbreviations
Part II—Syntheses and Examples
Part III—Pharmacology and Biological Assays
Part IV—Tables
Part V—Pharmaceutical Compositions

Part I—Glossary of Terms and Abbreviations

In order to remove any ambiguity which may exist with respect to the meanings of certain terms and abbreviations which are used herein, the following glossary is provided. Generally, the below provided meanings are typically well-known in the art, and are consistent with art-recognized usages.

BCECF: 2',7'-bis-(2-carboxyethyl)-5 (and 6)-carboxyfluorescein
DIEA: Diisopropyl amine
DME: Dulbecco's Modified Eagles Media
DMEM-HSA: Dulbecco's Modified Eagles Media with 2.5 mg/ml Human Serum Albumin
DMF: Dimethyl formamide
ECS: Endothelial cells
EDC: 1-Ethyl-3-(3' diethylaminopropyl)-carbodiimide
EtOAc: Ethyl Acetate
HBSS: Hank's Balanced Salts Solution
HSA: Human Serum Albumin
$IC_{50}$: Inhibitory concentration, concentration at which adhesion is inhibited to 50% of control level.
MeOH: Methanol
PBS: Phosphate Buffered Saline
TFA: Trifluoroacetic acid
TFAA: Trifluoroacetic anhydride
TNFα: Tumor Necrosis Factor-Alpha

Part II—Syntheses and Examples

The compounds of the present invention can be prepared using chemical techniques and reactions which are well known in the art. For example a coupling reaction of an appropriate amine with an appropriate substituted or unsubstituted naphthalene-, quinoline- or isoquinoline sulfonylchloride intermediate can provide a desired compound of Formula (I). In this respect, see the coupling reaction procedures set forth in Example 1 and/or Example 5 hereof. Overall, it is noted that starting compounds used to prepare the Formula (I) compounds are commercially available. However, if desired such compounds can also be manufactured using techniques well known in the chemical synthesis arts.

The following synthesis examples are provided as an aid to those desiring to practice the present invention as broadly disclosed herein. Typical syntheses are illustrated below.

SYNTHESIS OF SULFONAMIDES (a) Example 3

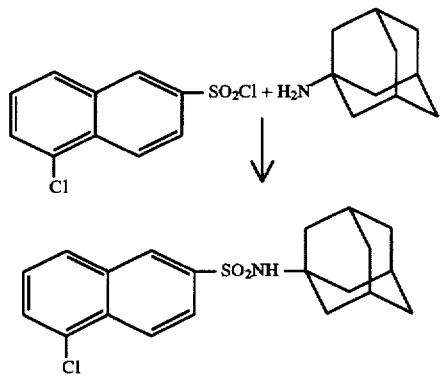

1-(5-Chloro-2-naphthylsulfonyl)-1-aminoadamantane (b) Example 5

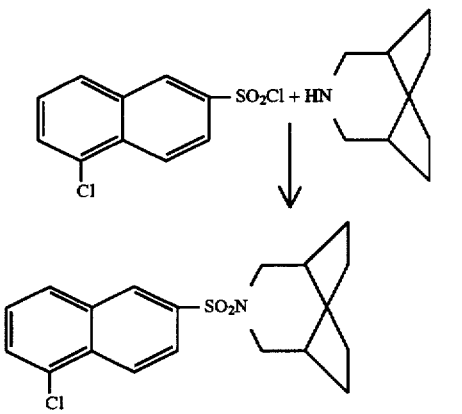

3-(5-Chloro-2-naphthylsulfonyl)-3-azabicyclo [3.2.2]nonane (c) Example 18

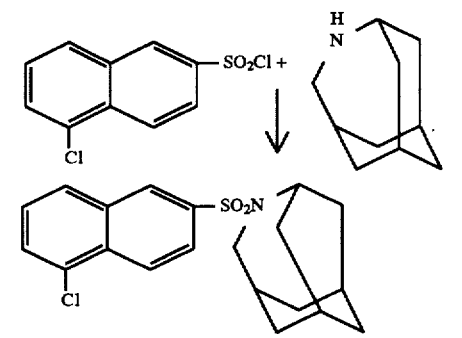

4-(5-Chloro-2-naphthylsulfonyl)-4-azahomoadamantane

-continued
SYNTHESIS OF SULFONAMIDES (d) Examples 50 and 51

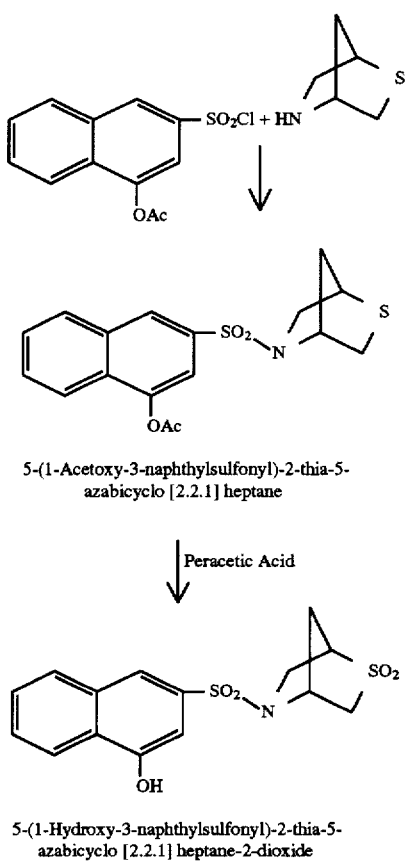

5-(1-Acetoxy-3-naphthylsulfonyl)-2-thia-5-azabicyclo [2.2.1] heptane

Peracetic Acid 5-(1-Hydroxy-3-naphthylsulfonyl)-2-thia-5-azabicyclo [2.2.1] heptane-2-dioxide

EXAMPLE 1

N-Cyclohexyl-5-chloro-2-naphthalenesulfonamide

The title compound was prepared from the coupling of cyclohexylamine and 5-chloro-2-naphthalenesulfonyl chloride. Cyclohexylamine (1.0 g, 3.8 mmol) and diisopropyl ethylamine (1.35 ml, 7.7 mmol) were dissolved in 30 ml chloroform. 5-Chloro-1-naphthalenesulfonyl chloride (0.88 m., 7.7 mmol) in 20 ml chloroform was added dropwise to the solution. After stirring overnight, the CHCl$_3$ solution was washed with saturated sodium bicarbonate solution and brine. Drying over magnesium sulfate and evaporation of the CHCl$_3$ followed by recrystallization with isopropyl ether/methanol gave 0.92 g (75% yield) of a yellow solid: mp 133°–134° C.; $^1$H NMR (CDCl$_3$): 8.48 (d, J=1.8, 1 H, H1), 8.38 (d, J=9.0, 1 H, H3), 8.00 (d, J=9.0, 1 H, H4), 7.88 (d, J=8.3, 1 H, H6), 7.71 (d, J=7.5, 1 H, H8), 7.51 (t, J=7.8, 1 H, H7), 5.07 (d, J=7.7, 1 H, NH), 3.23–3.15 (m, 1 H, NHCH, 1.77–1.72 (m, 2 H, ring H's), 1.61–1.55 (m, 2H, ring H's), 1.51–1.45 (m, 1H, ring H), 1.22–1.10 (m, 6H ring H's); anal. calcd. for C$_{16}$H$_{18}$NO$_2$SCl; C, 59.34; H, 5.60; N, 4.33; found: C, 59.27; H, 5.60; N, 4.30.

EXAMPLE 2

N-Phenyl-5-chloro-2-naphthalenesulfonamide

The title compound was prepared using a procedure similar to the procedure used to prepare Example 1. From 1 g (3.8 mmol) of 5-chloro-2-naphthalenesulfonyl chloride and 0.70 ml (7.6 mmol) of aniline, there was obtained a yellow solid. Recrystallization with isopropyl ether/methanol gave brown crystals, 1 g (83% yield): mp 181°–183° C.; $^1$H-NMR (CDCl$_3$): 8.35 (d, J=1.8, 1 H, H1), 8.31 (d, J=9.0, 1 H, H3), 7.85 (d, J=9.0, 1 H, H4), 7.79 (d, J=8.3, 1 H, H6), 7.69 (d, J=7.5, 1 H, H8), 7.48 (t, J=7.9, 1 H, H7), 7.25–7.19 (m, 2 H, aryl H's), 7.13–7.06 (m, 3 H, aryl, H's), 6.93 (s, 1 H, NH).

EXAMPLE 3

1-(5-Chloro-2-naphthylsulfonyl)-1-aminoadamantane

The title compound was prepared using a procedure similar to the procedure used to prepare Example 1. 1.0 g (3.8 mmol) of 5-chloro-2-naphthalenesulfonyl chloride and 1.15 g (7.6 mmol) of 1-adamantane amine afforded the product. Recrystallization with ethyl acetate gave a yellow solid, 0.81 g (58% yield): mp 202°–204° C.; $^1$H NMR (CDCl$_3$): 8.47 (d, J=1.8, 1 H, H1), 8.37 (d, J=9.1, 1 H, H3), 7.99 (d, J=9.0, 1 H, H4), 7.88 (d, J=8.2, 1 H, H6), 7.71 (d, J=7.5, 1 H, H8), 7.51 (t, J=7.9, 1 H, H7), 4.82 (s, 1 H, NH), 1.99 (br. s, 3 H, alkyl H's), 1.85–1.80 (m, 6 H, alkyl H's), 1.59–1.50 (m, 6 H, alkyl H's); anal. calcd. for C$_{20}$H$_{22}$NO$_2$SCl: C, 63.90; H, 5.90; N, 3.73; found: C, 63.97; H, 5.93; N, 370.

EXAMPLE 4

1-(5-Chloro-2-naphthylsulfonyl)-1-phenyl-1,3-diaminopropane

To a mixture of N-phenyl-N(3-propanol)-5-chloro-2-naphthalenesulfonamide (1.38 mm, 0.52 g), phthalimide and PPh$_3$ (1.66 mm, 0.435 g) in 7 ml dry THF was added DIEA (1.5 mm, 0.2 ml) in 3 ml dry THF, and the mixture was stirred overnight. The solvent was evaporated, and the residue was triturated with Et$_2$O to give a precipitate which was filtered to give a white powder and yellow filtrate. The powder (0.44 g) was PPh$_3$O. The filtrate was evaporated and the residue was suspended in 6 ml EtOH. Hydrazine monohydrate was added which resulted in gas evolution and loss of some color. The solution was brought to reflux and maintained for 2 hours. A precipitate formed at initial reflux. It was then cooled to room temperature and filtered. The solvent was evaporated to give a yellow oil (0.90 g), which was purified by chromatography to give 18 mg of a yellow powder, mp: 109°–112° C.

EXAMPLE 5

3-(5-Chloro-2-naphthylsulfonyl)-3-azabicyclo[3.2.2]nonane

The title compound was prepared from the coupling of 3-azabicyclo[3.2.2]nonane and 5-chloro-2-naphthalenesulfonyl chloride. 3-Azabicyclo[3.2.2]nonane (0.31 g, 2.5 mmol) and diisopropyl ethyl amine (1.0 ml, 5.7 mmol) were dissolved in 10 ml chloroform. 5-Chloro-1-naphthalenesulfonyl chloride (0.50 g, 1.9 mmol) in 20 ml chloroform was added dropwise to the solution. After stirring overnight, the solution was washed with saturated sodium bicarbonate solution and brine. Drying over magnesium sulfate and evaporation followed by recrystallization with isopropyl ether/methanol gave 0.50 g (76% yield) of a yellow solid: mp 138°–139° C.; $^1$H NMR (CDCl$_3$): 8.39 (d, J=8.9, 1 H, H3), 8.33 (d, J=1.7, 1 H, H1), 7.91–7.84 (m, 2

H, H4 and H6), 7.72 (d, J=7.5, 1 H, H8), 7.52 (t, J=7.9, 1 H, H7), 3.31 (d, J=4.2, 4 H, N (CH$_2$R)$_2$), 2.09 (s, 2 H, N(CH$_2$CHR)$_2$), 1.75–1.61 (m, 8 H, alkyl H's); anal calcd for C$_{18}$H$_{20}$ $_2$NO$_2$SCl; C, 61.79; H, 5.76; N, 4.00; found: C, 61.89; H, 5.80; N, 4.08.

EXAMPLE 6

2-(5-Chloro-2-naphthylsulfonyl)-2-(3-aminopropyl)-2-aminoadamantane

5-Chloro-N-(2-adamantyl)-N-(3-hydroxypropyl)-2-naphthalene sulfonamide (300 mg, 0.69 mmol) was combined with phthalimide (107 mg, 0.73 mmol), and triphenylphosphine (190 mg, 0.73 mmol) in dry THF (5 ml). This solution was added dropwise to a solution of diethylazodicarboxylate (0.2 ml, 1.46 mmol) in THF (3 ml), and the mixture was stirred at room temperature for 40 hours. At this time, the solvent was evaporated, and the residue was taken up in 30% EtOAc in hexane. Precipitation of the product was induced by scratching with a glass rod. The white solid was collected by filtration. Analysis of the product by thin layer chromatography indicated no triphenylphosphine oxide to be present. This intermediate (380 mg) was suspended in EtOH (20 ml), and then hydrazine (0.1 ml, 2.07 mmol) was added. The suspension was heated at reflux for 4 hours, and the resulting colorless solution was concentrated to provide a white solid, which was purified by chromatotron using 15% MeOH in CHCl$_3$ to provide a pale yellow oil. The hydrochloride salt was prepared using anhydrous HCl in EtOAc, and precipitation was induced by addition of Et$_2$O to provide a tan solid (65 mg)(mp. 130°–145° C., dec.): $^1$H NMR (CDCl$_3$) δ 1.46 (2H, m, 2×CH), 1.58–1.82 (11H, m, alkyl), 1.89 (2H, m CH$_2$), 2.22 (2H, br s, CH$_2$), 2.42 (2H, br s, CH$_2$N), 2.88 (3H, br s, NH$_3$), 3.54 (2H, t, J=18.8 Hz, CH$_2$N), 3.62 (1H, br s, CHN), 7.48 (1H, t, J =7.9 Hz, ArH), 7.68 (1H, d, J=6.6 Hz, ArH), 7.88 (2H, m, ArH), 8.33 (1H, d, J=12.5 Hz, ArH), 8.40 (1H, d, J=1.63 Hz, ArH).

EXAMPLE 7

2-(5-Chloro-2-naphthylsulfonyl)-2-aminoadamantane

The title compound was prepared using a procedure similar to the procedure used to prepare Example 1. 2-Adamantanamine, 0.71 g (3.8 mmol) and 0.5 g (1.9 mmol) of 5-chloro-2-naphthalenesulfonyl chloride gave an off-white solid, 0.70 g. Recrystallization with ethyl acetate gave a yellow solid, 0.41 g (57% yield): mp 206°–207° C., $^1$H NMR (CDCl$_3$): 8.47 (d, J=1.8, 1 H, H1), 8.83 (d, J=8.9, 1 H, H3), 7.98 (d, J=9.0, 1H, H4), 7.88 (d, J=8.3, 1 H, H6), 7.72 (d, J=7.5, 1 H, H8), 7.52 (t, J=7.9, 1 H, H7), 5.24 (d, J=7.6, 1 H, NH), 3.50–3.45 (m, 1H, NHCHR), 1.83–1.51 (m, 14h, Alkyl H's); anal. calcd for C$_{20}$H$_{22}$NO$_2$SCl: C, 63.90; H, 5.90; N, 3.73; found: C, 64.02; H, 5.88; N, 3.73.

EXAMPLE 8

N-[(R)(+)-Bornyl]-5-chloro-2-naphthalenesulfonamide

The title compound was prepared using a procedure similar to the procedure used to prepare Example 1. (R)(+)Bornylamine, 0.50 g (3.3 mmol) and 0.50 g (1.9 mmol) of 5-chloro-2-naphthalenesulfonyl chloride produced 0.80 g of a yellow solid. Recrystallization with isopropyl ether/methanol gave a yellow solid 0.39 g (54% yield): mp 195.6°–197.6° C.; $^1$H NMR (CDCl$_3$): 8.46 (d, J=1.8, 1 H, H1), 8.38 (d, J=9.0, 1 H, H3), 7.98 (d, J=9.0, 1H H4), 7.87 (d, J=8.2, 1 H, H6), 7.72 (d, J=7.3, 1H, H8), 7.51 (5, J=7.9, 1 H, H7), 5.03 (d, J=9.5, 1H, NH), 3.55–3.48 (m, 1 H, NHCHR), 2.03–1.93 (m, 1 H, alkyl H), 1.73–1.63 (m, 1 H, alkyl H), 1.58–1.50 (m, 2 H, alkyl H's), 1.42–1.30 (m, 1H, alkyl H), 1.18–1.08 (m, 1 H, alkyl H), 0.81 (s, 3 H, CH$_3$), 0.78 (s, 3 H, CH$_3$), 0.74 (s, 3 H, CH$_3$), 0.73–0.68 (m, 1 H, alkyl H); anal. calcd. for C$_{20}$H$_{24}$NO$_2$SCl: C, 63.56; H, 6.40; N, 3.71; found: C, 63.59; H, 6.43; N, 3.76.

EXAMPLE 9

1-(5-Chloro-2-naphthylsulfonyl)-1-aminomethyladamantane

The title compound was prepared using a procedure similar to the procedure used to prepare Example 1. Reaction of 0.50 ml (2.85 mmol) of 1-adamantanemethylamine and 0.50 g (1.9 mmol) of the sulfonylchloride yielded 0.81 g of an off-white solid. Recrystallization with chloroform gave a yellow solid, 0.41 g (55% yield): mp 204.5°–206.5° C., $^1$H NMR (CDCl$_3$): 8.43 (d, J=1.8, 1 H, H1), 8.40 (d, J=9.0, 1 H, H3), 7.93 (d, J=9.0, 1 H, H4), 7.89 (d, J=8.4, 1 H, H6), 7.73 (d, J=7.5, 1 H, H8), 7.53 (5, J=7.9, 1 H, H7), 4.58 (t, J=6.7, 1 H, NH), 2.61 (d, J=6.8, 2 H, NHCH$_2$R), 1.95 (br. s, 3 H, alkyl H's), 1.72–1.68 (m, 3 H, alkyl H's), 1.60–1.55 (m, 3 H, alkyl H's), 1.482–1.45 (m, 6 H, alkyl H's); anal. calcd. for C$_{21}$H$_{24}$NO$_2$SCl: C, 64.68; H, 6.20; N, 3.59; found: C, 64.60; H, 6.23; N, 3.63.

EXAMPLE 10

1-(2-Naphthylsulfonyl)-1-aminoadamantane

The title compound was prepared using a procedure similar to the procedure used to prepare Example 1. The 2-naphthalenesulfonyl chloride, 0.50 g (2.2 mmol) when reacted with 0.40 g (2.6 mmol) of 1-adamantanamine gave an off-white foam. Recrystallization with isopropyl ether/methanol gave brown crystals, 0.40 g (53% yield): mp 173°–176° C.; $^1$H NMR (CDCl$_3$): 8.48 (s, 1 H, H1), 7.98–7.88 (m, 4 H, aromatic H's), 7.65–7.58 (m, 2 H, aromatic H's), 4.73–4.65 (m, 1 H, NH), 1.95 (br. s, 3 H, alkyl H's), 1.85–1.78 (m, 6H, alkyl H's), 1.60–1.50 (m, 6 H, alkyl H's); anal. calcd. for C$_{20}$H$_{23}$NO$_2$S: C, 70.35; H, 6.79; N, 4.10; found: C, 70.22; H, 6.78; N, 4.05.

EXAMPLE 11

3-(5-Chloro-2-naphthylsulfonyl)-3-aminonoradamantane

The title compound was prepared using a procedure similar to the procedure used to prepare Example 1. Coupling 0.50 g (1.9 mmol) of the sulfonylchloride with 0.43 g (2.5 mmol) of 3-noradamantane amine gave a yellow oil. Recrystallization with isopropyl ether/methanol gave a yellow solid, 0.36 g (52% yield): mp 152°–155° C.; $^1$H NMR (CDCl$_3$); 8.47 (d, J=1.8, 1 H, H1), 8.38 (d, J=9.0, 1 H, H3), 7.99 (d, J=9.0, 1 H, H4), 7.88 (d, J=8.3, 1 H, H6), 7.71 (d, J=7.5, 1 H, H8), 7.51 (t, J=7.9, 1 H, H7), 5.11–5.05 (m, 1 H, NH), 2.33–2.28 (m, 1 H, alkyl H), 2.18 (br. s, 2 H, alkyl H's), 1.90–1.78 (m, 7 H, alkyl H's), 1.56–1.38 (m, 3 H, alkyl H's); anal. calcd. for C$_{19}$H$_{20}$NO$_2$SCl: C, 63.06; H, 5.57; N, 3.87; found: C, 62.90; H, 5.55; N, 3.85.

EXAMPLE 12

3-(5-Chloro-2-naphthylsulfonyl)-3-aminoquinuclidine

The title compound was prepared using a procedure similar to the procedure used to prepare Example 5. 3- aminoquinuclidine#2HCl, 0.5 g (2.5 mmol) and the sulfonylchloride gave 0.60 g of a white solid. Trituration with chloroform followed by ethyl ether gave a white solid, 0.48 g (72% yield): mp 299°–305° C. (dec); $^1$H NMR (DMSO): 7.72 (d, J=1.8, 1 H, H1), 7.63 (d, J=9.0, 1 H, H3), 7.25–7.18 (m, 2 H, H4 and H6), 7.01–6.98 (m, 1 H, H8), 6.80 (t, J=7.9, 1 H, H7), 2.92–2.82 (m, 1 H, SO$_2$NH$\underline{CH}$R), 2.79–2.70 (m, 1 H, alkyl H), 2.45–2.24 (m, 4 H, alkyl H's), 1.41–1.27 (m, 1 H, alkyl H), 1.23–0.95 (m, 5 H, alkyl H's).

EXAMPLE 13

3-(2-Naphthylsulfonyl)-3-azabicyclo[3.2.2]nonane

The title compound was prepared using a procedure similar to the procedure used to prepare Example 5. 2-Naphthalenesulfonyl chloride, 0.50 g (2.2 mmol) and 0.36 g (2.9 mmol) of 3-azabicyclo[3.2.2]nonane produced the desired product. Recrystallization with isopropyl ether/methanol gave an amber solid, 0.47 g (68% yield): mp 149°–150° C.; $^1$H NMR (CDCl$_3$): 8.34 (s, 1 H, H1), 7.99–7.92 (m, 3 H, aryl H's), 7.77–7.74 (m, 1 H, aryl H), 7.67–7.59 (m, 2 H, aryl H's); 3.30 (d, J=4.2, 4 H, SO$_2$N($\underline{CH_2}$R)$_2$), 1.99 (s, 2 H, SO$_2$N(CH$_2$$\underline{CHR}$)$_2$), 1.73–1.57 (m, 8 H, alkyl H's); anal calcd. for C$_{18}$H$_{21}$NO$_2$S: C, 68.54; H, 6.71; N, 4.44; found: C, 68.67; H, 6.75; N, 4.47.

EXAMPLE 14

N-(1-Hydroxy-3-naphthalylsulfonyl)-O-benzyl-4-hydroxyproline

N-(1-acetoxy-3-naphthalylsulfonyl)-O-benzyl-4-hydroxyproline methyl ester (101 mg, 0.23 mmol) was dissolved in MeOH (20 ml) and NaOH (19 mg) in water (3 ml) was added and the mixture was maintained for 3 hr. At this time the solvent was evaporated under reduced pressure and the residue was partitioned between CHCl$_3$ and 1N aqueous HCl. The CHCl$_3$ phase was dried over Na$_2$SO$_4$ then concentrated. The residue was purified by flash chromatography using 5% MeOH in CHCl$_3$. The pure product was obtained as a white foam: $^1$H NMR (DMSO d$_6$) δ 1.61 (1H, br m, ½ CH$_2$), 2.19 (1H, br m, ½ CH$_2$), 3.22 (1H, br m, ½ CH$_2$N), 3.61 (1H, br m, ½ CH$_2$N), 4.15 (1H, br m, CHN), 4.20 (2H, s, CH$_2$Ar), 6.70 (1H, s, ArH), 7.01 (2H, br s, ArH), 7.09–7.21 (3H, m, ArH), 7.25–7.48 (3H, m, ArH), 7.69 (1H, d, J=8.15, ArH), 8.27 (1H, d, J=8.07, ArH).

EXAMPLE 15

1-(5-Acetoxy-2-naphthylsulfonyl)-1-aminoadamantane

The title compound was prepared using a procedure similar to the procedure used to prepare Example 5. 1-adamantanamine, 0.61 g (4.0 mmol) and 0.50 g (2.0 mmol) of 5-acetoxy-2-naphthalenesulfonyl chloride gave 0.78 g of a green foam. Purification by chromatotron using 2/1 hexane/ethyl acetate gave a green solid, 0.18 g (25% yield): mp 247°–249° C.; $^1$H NMR (CDCl$_3$): 8.40 (d, J=1.8, 1 H, H1), 8.30 (d,J=8.9, 1 H, H3), 7.84 (d, J=9.0, 1 H, H4), 7.54 (d, J=8.1, 1 H, H6), 7.42 (t, J=7.9, 1 H, H7), 6.95 (d, J=7.6, 1 H, H6), 5.45 (s, 1 H, NH), 1.99 (s, 3 H, alkyl H's), 1.82–1.79 (m, 6 H, alkyl H's), 1.54–1.50 (m, 9 H, alkyl H's and CH$_3$). Anal. calcd. for C$_{22}$H$_{25}$NO$_4$S: C, 66.14; H, 6.31; N, 3.51. Found: C, 66.71; H, 6.49; N, 3.81.

EXAMPLE 16

3-(5-Chloro-1-naphthylsulfonyl)-3-azabicyclo[3.2.2] nonane

The title compound was prepared using a procedure similar to the procedure used to prepare Example 5. The CHCl$_3$ reaction of 0.26 g (1.0 mmol) of the sulfonylchloride and 0.16 g (1.3 mmol) of the azabicyclo compound yielded an orange oil, 0.38 g. Recrystallization with hexane gave a yellow solid, 0.25 g (71% yield): mp 105°–106° C.; $^1$H NMR (CDCl$_3$): 8.74 (d, J=8.6, 1 H, H8), 8.50 (d, J=8.5, 1 H, H4), 8.22 (d, J=7.4, 1 H, H2), 7.66–7.51 (m, 3 H, H3, H6 and H7), 3.39 (d, J=4.2, 4 H, SO$_2$N($\underline{CH_2}$R)$_2$), 2.03 (s, 2 H, SO$_2$N(CH$_2$2$\underline{CHR}$)$_2$), 1.68–1.57 (m, 8 H, alkyl H's); anal. calcd. for C$_{18}$H$_{20}$NO$_2$SCl: C, 61.79; H, 5.76; N, 4.00; found: C, 61.70; H, 5.75; N, 3.94.

EXAMPLE 17

3-(5-Chloro-2-naphthylsulfonyl)-3-azabicyclo[3.2.1]-octane

The title compound was prepared using a procedure similar to the procedure used to prepare Example 5. From 0.16 g (1.1 mmol) of the 3-azabicyclooctane and 0.26 g (1.0 mmol) of the sulfonylchloride and 0.52 ml of DIEA, there was obtained 0.32 g of a cream solid. Recrystallization with isopropyl ether/methanol gave an off-white solid, 0.19 g (58% yield): mp 137°–138° C.; $^1$H NMR (CDCl$_3$): 8.29 (d, J=9.0, 1 H, H3), 8.26 (d, J=1.6, 1 H, H1), 7.83 (d, J=8.2, 1 H, H4), 7.77 (d, J=8.9, 1 H, H6), 7.62 (d, J=7.4, 1 H, H8), 7.44 (t, J=7.9, 1 H, H7), 3.56–3.51 (m, 2 H, alkyl H's), 2.41 (d, J=10.6, 2 H, alkyl H's), 2.15 (s, 2 H, alkyl H's), 1.67–1.55 (m, 4 H, alkyl H's), 1.41–1.35 (m, 1 H, alkyl H), 1.09 (d, J=11.5, 1 H, alkyl H); anal. calcd. for C$_{17}$H$_{18}$NO$_2$SCl: C, 60.80; H, 5.40; N, 4.17; found: C, 60.74; H, 5.41; N, 4.16.

EXAMPLE 18

4-(5-Chloro-2-naphthylsulfonyl)-4-azahomoadamantane

The title compound was prepared using a procedure similar to the procedure used to prepare Example 5. 4-Azahomoadamantane, 0.167 g (1.1 mmol); 0.26 g (1.0 mmol) of the sulfonylchloride and 0.52 ml of DIEA afforded 0.40 g of pink oil. Recrystallization with isopropyl ether/methanol gave grey needles, 0.22 g (58% yield): mp 127°–128° C.; $^1$H NMR (CDCl$_3$): 8.34 (d, J=1.6, 1 H, H1), 8.27 (d, J=8.9, 1 H, H3), 7.86 (d, J=8.9, 1 H, H4), 7.80 (d, J=8.2, 1 H, H6), 7.58 (d, J=7.3, 1 H, H8), 7.41 (t, J=7.9, 1 H, H7), 4.46 (s, 1 H, SO$_2$N$\underline{CHR}$), 3.43 (d, J=3.7, 2 H, SO$_2$NCH$_2$R), 2.20–2.13 (m, 1 H, alkyl H), 1.82–1.72 (m, 6 H, alkyl H's), 1.41–1.33 (m, 6 H, alkyl H's); anal. calcd. for C$_{20}$H$_{22}$NO$_2$SCl: C, 63.90; H, 5.90; N, 3.73; found: C, 63.82; H, 5.91; N, 3.68.

EXAMPLE 19

2-(5-Chloro-2-naphthylsulfonyl)-2-azaadamantane

The title compound was prepared using a procedure similar to the procedure used to prepare Example 5. The azaadamantane 0.05 g (0.36 mmol) and the sulfonylchloride 0.09 g (0.36 mmol) along with DIEA gave 100 mg of a yellow solid. Purification by chromatotron using 4/1 hexane/ethyl acetate gave an off-white solid, 5 mg (5% yield): $^1$H NMR (CDCl$_3$): 8.42 (d, J=1.8, 1 H, H1), 8.35 (d, J=8.9, 1 H, H3), 7.99 (d, J=9.0, 1 H, H4), 7.86 (d, J=8.3, 1 H, H6), 7.68 (d, J=7.4, 1 H, H8), 7.48 (t, J=7.9, 1 H, H7), 4.63 (s, 1 H, alkyl H), 2.31–2.28 (m, 2 H, alkyl H's), 1.96–1.87 (m, 4 H, alkyl H's), 1.79–1.68 (m, 7 H, alkyl H's).

EXAMPLE 20

5-(5-Chloro-2-naphthylsulfonyl-2-thia-5-azabicyclo-2.2.1]heptane

The title compound was prepared using a procedure similar to the procedure used to prepare Example 5. From 0.3 g (2.0 mmol) the thiaazabicycloheptane, 0.5 g (1.9 mmol) of the sulfonylchloride and 0.66 ml of DIEA there was obtained a white foam, 0.61 g. Purification by chromatotron using 4/1 hexane/ethyl acetate gave a white solid, 0.21 g (32% yield): mp 161°–162° C.; $^1$H NMR (CDCl$_3$): 8.41 (s, 1 H, H1), 8.35 (d, J=8.9, 1 H, H3), 7.93–7.87 (m, 2 H, H4 and H6), 7.67 (d, J=7.5, 1 H, H8), 7.49 (t, J=7.9, 1 H, H7), 4.73 (s, 1 H, alkyl H), 3.65 (d, J=8.3, 1 H, alkyl H), 3.54–3.50 (m, 2 H, alkyl H's), 3.10 (d, J=10.1, 1 H, alkyl H), 2.95 (d, J=10.1, 1 H, alkyl H), 1.66 (qt, J=10.7, 36.0, 2 H, alkyl H's); anal. calcd. for C$_{15}$H$_{14}$NO$_2$S$_2$Cl: C, 53.01; H, 4.15; N, 4.12; found: C, 52.99; H, 4.20; N, 4.07.

EXAMPLE 21

5-(5-Chloro-2-naphthylsulfonyl)-2-oxa-5-azabicyclo-[2.2.1]heptane

The title compound was prepared using a procedure similar to the procedure used to prepare Example 5. Reaction of 0.5 g (1.9 mmol) of the sulfonylchloride with 0.27 g (2.0 mmol) of the azabicycloheptane produced a white foam, 0.62 g. Recrystallization with isopropyl ether/methanol gave a yellow solid, 0.38 g (61% yield): mp 132°–133° C.; $^1$H NMR (CDCl$_3$): 8.43 (d, J=1.2, 1 H, H1), 8.35 (d, J=8.9, 1 H, H3), 7.94 (d, J=8.9, 1 H, H4), 7.89 (d, J=8.2, 1 H, H6), 7.67 (d, J=7.4, 1 H, H8), 7.49 (t, J=7.8, 1 H, H7), 4.58 (s, 1 H, alkyl H), 4.48 (s, 1 H, alkyl H), 3.87 (d, J=7.8, 1 H, alkyl H), 3.70–3.67 (m, 1 H, alkyl H), 3.45 (d, J=9.8, 1 H, alkyl H), 3.28 (d, J-9.8, 1H alkyl H), 1.68 (d, J=10.2, 1 H, alkyl H), 1.28 (d, J=10.2, 1 H, alkyl H); anal. calcd. for C$_{15}$H$_{14}$NO$_3$SCl: C, 55.64; H, 4.36, N, 4.33; found: c, 55.52; H, 4.40; N, 4.37.

EXAMPLE 22

2-(5-Chloro-2-naphthylsulfonyl)-2,5-diazabicyclo-[2.2.1]heptane 2-(5-chloro-2-naphthylsulfonyl)-5-tertiary butoxy carbonyl-2,5-diazabicyclo[2.2.1] heptane (0.50 g, 2 mmol) was dissolved in about 5 ml. EtOAc. HCl gas was bubbled through the solution, resulting in an immediate change of color from orange to yellow. HCl was bubbled in for 15 minutes more and a precipitate started forming at this time. After 30 minutes, the ice bath was removed. The reaction was complete at 2 hours. The precipitate was filtered and triturated with Et$_2$O to give 0.37 g of an off-white powder, mp: 225°–2270° C.

EXAMPLE 23

2-(5-Chloro -2-naphthylsulfonyl)-5-methylformyl-2,5-diazabicyclo[2.2.1]heptane

The title compound was prepared from 2-(5-Chloro-2-naphthylsulfonyl)-2,5-diazabicyclo[2.2.1]heptane, by dissolving the heptane (0.29 g, 0.8 mmol) in 20 ml dioxane and 1 ml of 1N NaOH solution. The solution was cooled with an ice bath. Methyl chloroformate (0.062 ml, 0.8 mmol) was added dropwise. Additional 1N NaOH solution was added to keep the pH above 9. After 1 hour at room temperature, the solvent was evaporated. The residue was partitioned between chloroform and saturated sodium bicarbonate solution. The aqueous layer was extracted three times with chloroform. After drying over magnesium sulfate, the solvent was evaporated to give a yellow foam. This was purified by chromatotron using 3/2 hexane/ethyl acetate to give 0.27 g (87% yield) of a white solid: mp 151°–152° C.; $^1$H NMR (CDCl$_3$): 8.41-8-37 (m, 2 H, H1 and H3), 7.95-7-89 (m, 2 H, H4 and H6), 7.71 (d, J=7.4, 1 H, H8), 7.53 (t, J=7.8, 1 H, H7), 4.58 (s, 1 H, alkyl H), 4.49 (s, 1 H, alkyl H), 3.68 (s, 1 H, alkyl H), 3.55–3.46 (m, 4 H, alkyl H's), 1.70 (d, J=10.1, 1 H, alkyl H), 1.33–1.28 (m, 1 H, alkyl H).

EXAMPLE 24

1-(5-Chloro-2-naphthylsulfonyl)-1-amino-3-adamantane-carboxylic acid

The title compound was prepared by Schotten-Baumann coupling of 5-chloro-2-naphthalenesulfonyl chloride and 1-amino-3-adamantane carboxylic acid. Purification was achieved by basic extraction from ethyl acetate and precipitation with 1N HCl gave a white solid (5% yield): mp 255°–256° C.; $^1$H NMR (DMSO): 12.02 (s, 1 H, COOH), 8.55 (s, 1 H, H1), 8.35 (d, J=8.9, 1 H, H3), 8.19 (d, J=8.2, 1 H, H4), 8.05 (d, J=9.0, 1 H, H6), 7.88–7.8 (m, 2 H, H8 and NH), 7.65 (t, J=7.9, 1 H, H7), 2.00 (s, 2 H, alkyl H's), 1.83 (s, 2 H, alkyl H's), 1.66–1.55 (in, 8 H, alkyl H's), 1.46–1.39 (m, 2 H, alkyl H's).

EXAMPLE 25

4-(5-Chloro-2-naphthylsulfonyl)-1-hydroxy-4-azahomoadamantane

The title compound was prepared as using a procedure similar to the procedure used to prepare Example 5. The sulfonylchloride 0.091 g (0.35 mmol); 0.055 g (0.33 mmol) of 1-hydroxy-4-azahomoadamantane along with 0.122 ml of DIEA in CHCl$_3$ gave 130 mg of a yellow solid. Purification by chromatotron using 3/1 hexane/ethyl acetate gave a yellow solid, 28 mg (22% yield): mp 200°–202° C.; $^1$H NMR (CDCl$_3$): 8.44–8.39 (m, 2 H, H1 and H3), 7.94–7.88 (m, 2 H, H6 and H8), 7.73 (d, J=7.4, 1 H, H4), 7.53 (t, J=7.9, 1 H, H7), 4.53 (s, 1 H, OH), 2.74–2.68 (m, 2 H, alkyl H's), 2.46–2.36 (m, 3 H, alkyl H's), 2.28–2.18 (m, 2 H, alkyl H's), 2.09–1.93 (m, 2 H, alkyl H's), 1.88–1.69 (m, 2 H, alkyl H's), 1.66–1.47 (m, 2 H, alkyl H's), 0.91–0.83 (m, 2 H, alkyl H's).

EXAMPLE 26

3-(6-Isoquinolinesulfonyl)-3-azabicyclo[3.2.2]nonane

The title compound was prepared using a procedure similar to the procedure used to prepare Example 5. The isoquinolinesulfonyl chloride, 0.5 g (2.2 mmol) together with 0.43 g (3.3 mmol) of the azabicyclononane and 1.0 ml of DIEA gave 330 mg of yellow oil. Purification by chromatotron using 4/1 chloroform/ethyl acetate gave a yellow solid, 120 mg (17% yield): mp 136°–137° C.; $^1$H NMR (CDCl$_3$): 9.34 (s, 1 H, H1), 8.68 (d, J=6.1, 1 H, H3), 8.34 (d, J=7.4, 1 H, H6), 8.19 (d, J=8.2, 1 H, H8), 7.70 (t, J=7.8, 1 H, H7), 3.41–3.38 (m, 4 H, N(CH$_2$CHR)$_2$), 2.08 (s, 2 H, N(CH$_2$CHR)$_2$) 1.70–1.61 (m, 8 H, alkyl H's).

EXAMPLE 27

1-(5-Chloro-2-naphthylsulfonyl)-1-amino-2-oxaadamantane

The title compound was prepared using a procedure similar to the procedure used to prepare Example 5. 0.14 g (0.50 mmol) of the sulfonylchloride, 0.07 g (0.46 mmol) of the amino-2-oxaadamantane with 0.26 ml DIEA reacted in CHCl$_3$ to produce 0.19 g of orange oil. Purification by chromatotron using 12/1/1 hexane/acetone/chloroform gave a yellow solid, 6 mg: mp 95°–97° C.; $^1$H NMR (CDCl$_3$): 8.41 (d, J=1.6, 1 H, H1), 8.37 (d, J=8.9, 1 H, H3), 7.92–7.86 (m, 2 H, H4 and H6), 7.71 (d, J=7.4, 1 H, H8), 7.51 (t, J=7.4, 1 H, H7), 4.22–4.13 (m, 1 H, alkyl H), 3.26 (qt, J=14.2, 2 H, alkyl H's), 1.30 (t, J=7.1, 4 H, alkyl H's), 1.07 (d, J=6.8, 6 H, alkyl H's).

EXAMPLE 28

4-(5-Chloro-2-naphthylsulfonyl)-4-amino-1-azaadamantane

The title compound was prepared using a procedure similar to the procedure used to prepare Example 5. Purification by chromatotron using 12/1/1 chloroform/acetone/methanol gave a yellow solid: $^1$H NMR (CDCl$_3$): 8.60 (d, J=1.6, 1 H, H1), 8.39 (d, J=8.9, 1 H, H3), 8.06 (d, J=8.8, 1 H, H4), 7.92 (d, J=8.1, 1 H, H6), 7.74 (d, J=7.6, 1 H, H8), 7.54 (t, J=7.9, 1 H, H7), 3.44–3.40 (m, 1 H, alkyl H), 3.31–3.05 (m, 4 H, alkyl H's), 2.48 (s, 1 H, alkyl H), 2.10–1.79 (m, 6 H, alkyl H's).

EXAMPLE 29

3-(6-Quinolinesulfonyl)-3-azabicyclo[3.2.2]nonane

The title compound was prepared using a procedure similar to the procedure used to prepare Example 5. The quinolinesulfonyl chloride, 0.48 g (2.1 mmol) was reacted with 0.32 g (2.5 mmol) of the azabicyclononane in CHCl$_3$ with DIEA, 1.1 ml, as a base. The usual work-up afforded 0.53 g of an orange oil. Purification by column using 3/2 hexane/ethyl acetate gave a yellow solid, 0.38 g (58% yield): mp 124°–127° C.; $^1$H NMR (CDCl$_3$): 9.07–9.04 (m, 1 H, H2), 8.32 (d, J=1.8, 1 H, H5),8.29 (d, J=8.6, 1 H, H3), 8.23 (d, J=8.9, 1 H, H8), 8.00 (d, J=8.9, 1 H, H7), 7.54 (d, J=8.3, 1 H, H4), 3.33 (d, J=4.2, 4 H, N(CH$_2$R)$_2$), 2.10 (s, 2 H, N(CH$_2$CHR)$_2$) 1.75–1.61 (m, 8 H, alkyl H's). $^{13}$C NMR (CDCl$_3$): 150.48 (59, C9), 138.52 (333, C3), 137.20 (49, C10), 132.07 (322, C8), 129.62 (323, C5), 128.63 (109, C6), 127.61 (274, C7), 123.86 (305, C4), 56.17 (525, N(CH$_2$R)$_2$), 31.43 (388, N(CHCHR)$_2$), 25.95 (1000, other C's).

EXAMPLE 30

1-(6-Quinolinesulfonyl)-1-aminoadamantane

The title compound was prepared using a procedure similar to the procedure used to prepare Example 5. An orange solid, 0.67 g, was obtained from the reaction of 0.43 g (1.9 mmol) of the sulfonylchloride with 0.35 g (2.4 mmol) of the aminoadamantane. Purification by column using 3/2 hexane/ethyl acetate gave a yellow solid, 0.24 g (32% yield): mp 210°–212° C.; $^1$H NMR (CDCl$_3$): 9.06–9.04 (m, 1 H, H2), 8.52 (d, J=1.5, 1 H, H5), 8.30 (d, J=8.3, 1 H, H3), 8.25–8.18 (m, 2 H, H7 and H 8), 7.53 (d, J=8.3, 1 H, H4), 5.62 (s, 1 H, NH), 1.98 (s, 3 H, alkyl H's), 1.85–1.80 (m, 6 H, alkyl H's), 1.58–1.50 (m, 6 H, alkyl H's).

EXAMPLE 31

4-(6-Quinolinesulfonyl)-4-azahomoadamantane

The title compound was prepared using a procedure similar to the procedure used to prepare Example 5. 0.60 g of yellow solid was obtained by reacting 0.43 g (1.9 mmol) of the sulfonylchloride with 0.39 g (2.5 mmol) of the adamantane compound and 1.0 ml of DIEA. Purification by column using 3/2 hexane/ethyl acetate gave a yellow solid, 0.36 g (55% yield): mp 143°–145° C.; $^1$H NMR (CDCl$_3$): 9.06–9.04 (m, 1 H, H2), 8.42 (d, J=1.5, 1 H, H5), 8.33 (d, J=8.0, 1 H, H3), 8.23 (d, J=8.9, 1 H, H8), 8.08 (d, J=8.9, 1 H, H7), 7.55 (d, J=8.3, 1 H, H4), 4.54 (s, 1 H, NCHR), 3.52 (d, J=3.6, 2 H, NCH$_2$R), 2.28 (s, 1 H, alkyl H), 1.93–1.80 (m, 6 H, alkyl H's), 1.49–1.40 (m, 6 H, alkyl H's).

EXAMPLE 32

3-(1-Acetoxy-3-naphthylsulfonyl)-3-azabicyclo[3.2.2]nonane

4-Acetoxy-2-naphthalenesulfonyl chloride (861 mg, 3.02 mmol) and 3-azabicyclo[3.2.2]nonane (379 mg, 3.02 mmol) were combined in CHCl$_3$ (20 ml) and pyridine (20 ml), and the mixture was stirred at room temperature for 15 hours. At this time, the solvent was evaporated under reduced pressure and the residue was partitioned between EtOAc and 1N aqueous HCl. The EtOAc was then washed with saturated aqueous NaHCO$_3$, dried over Na$_2$SO$_4$ and concentrated. The residue was purified by flash chromatography using 1% acetone in CHCl$_3$ to provide 712 mg of the pure white product as a white foam: $^1$H NMR (CDCl$_3$) δ 1.52–1.84 (9H, m, 4×CH$_2$), 2.02–2.13 (2.H, br s, 2×CH) 2.46 (3H, s, CH$_3$CO), 3.31 (4H, d, J=4.2 Hz, 2×CH$_2$), 7.56–7.71 (3H, m, ArH), 7.92–8.02 (2H, m ArH).

EXAMPLE 33

3-(5-Chloro-2-naphthylsulfonyl)-1-hydroxy-3-aminoadamantane

The title compound was prepared using a procedure similar to the procedure used to prepare Example 5. The usual reaction between 1.05 g (4 mmol) of the 5-chloro-2-naphthalenesulfonyl chloride and 1.11 g (6 mmol) of the hydroxyaminoadamantane afforded 1.4 g of a brown oil. Purification by chromatotron using 1/1 hexane/ethyl acetate gave a yellow solid, 0.5 g (32% yield): mp 210°–212° C.; $^1$H NMR (CDCl$_3$): 8.46 (d, J='0.7, 1 H, H1), 8.39 (d, J=8.9, 1 H, H3), 7.95 (d,J=9.0, 1 H, H4), 7.89 (d, J=8.2, 1 H, H6), 7.72 (d, J=7.5, 1 H, H8), 7.52 (t, J=7.9, 1 H, H7), 4.61 (s, 1 H, NH), 2.20 (s, 2 H, alkyl H's), 1.81–1.75 (m, 6 H, alkyl H's), 1.53–1.45 (m, 6 H, alkyl H's ).

EXAMPLE 34

3-[(N-9-Fluorenylmethoxycarbonyl)-5-amino-2-naphthylsulfonyl]-3-azabicyclo[3.2.2]nonane The title compound was prepared using a procedure similar to the procedure used to prepare Example 5. 0.69 (1.5 mmol) of the FMOC sulfonyl chloride with 0.58 g (4.5 mmol) of the bicyclononane gave 0.79 g of tan solid after work-up of the reaction. Purification by chromatotron using 40/1 dichloromethane/ethyl acetate gave a yellow solid, 0.33 g (40% yield): $^1$H NMR (CDCl$_3$): 7.98–7.94 (m, 1 H), 7.84–7.75 (m, 5 H), 7.65–7.55 (m, 3 H), 7.44–7.39 (m, 3 H), 7.33–7.28 (m, 2 H), 6.94 (s, 1 H, NH), 4.64–4.59 (m, 2 H, COOCH$_2$R), 4.28 (s, 1 H, COOCH$_2$CHR), 3.33–3.28 (m, 4 H, N(CH$_2$R)$_2$), 2.09 (s, 2 H, N (CH$_2$CHR)$_2$), 1.72–1.55 (m, 8 H, alkyl H's).

EXAMPLE 35

3-(5-Amino-2-naphthylsulfonyl)-3-azabicyclo[3.2.2]nonane 0.33 g (0.6 mmol) of the product from Example 34 was dissolved in 10 ml of THF. 1.2 ml (1.2 mmol) of tetrabutylammonium fluoride (1M in THF, Aldrich) was added.

After 15 minutes, the solvent was evaporated, the residue dissolved in CHCl₃, and the solution was washed with brine and NaHCO₃ solution. The CHCl₃ was evaporated to an orange oil. The product was isolated as the HCl salt by treatment with HCl/EtOAc followed by trituration with diethyl ether which gave a tan solid, 90 mg (50% yield): ¹H NMR (DMSO): 8.48–8.35 (m, 2 H), 7.80–7.70 (m, 2 H), 7.58–7.53 (m, 1 H), 6.93–6.88 (m, 1 H), 3.24–3.20 (m, 4 H, N(CH₂R)₂), 2.06 (s, 2 H, N(CH₂CHR)₂), 1.63–1.52 (m, 8 H, alkyl H's).

EXAMPLE 36

6-(5-Chloro-2-naphthylsulfonyl)-6-amino-1-hydroxy-2-azahomoadamantane

The title compound was prepared by first suspending N-(1-Hydroxy-3-adamantyl)-5-chloro-2-naphthalene sulfonamide in 5 ml chloroform. Sulfuric acid (4 ml) was added and the mixture was cooled with an ice bath. Sodium azide (0.16 g, 2.3 mmol) was added in portions over thirty minutes. After stirring at room temperature for two hours, the mixture was poured onto ice-water. The aqueous layer was made basic with 1N NaOH solution and the product was extracted with chloroform. After drying over sodium sulfate, the solvent was evaporated to give a yellow foam. This was purified by chromatotron using 20/1 chloroform/methanol which gave a white solid (0.23 g, 48% yield): ¹H NMR (CDCl₃): 8.48 (d, J=1.7, 1 H, H1), 8.36 (d, J=9.0, 1 H, H3), 7.99 (d, J=9.0, 1 H, H4), 7.87 (d, J=8.2, 1 H, H6), 7.70 (d, J=7.4, 1 H, H8), 7.50 (t, J=7.9, 1 H, H7), 5.38 (s, 1 H, NH), 2.97–2.85 (m, 2 H, alkyl H's), 2.18–2.02 (m, 4 H, alkyl H's), 1.90–1.78 (m, 4 H, alkyl H's), 1.67–1.63 (m, 3 H, alkyl H's), 1.48–1.42 (m, 1 H, alkyl H).

EXAMPLE 37

1-(1,2,3,4-Tetrahydro-6-quinolinesulfonyl)-1-aminoadamantane

The title compound was prepared from the title compound of Example 30 following the procedure described by T. S. Hamilton and Roger Adams (J. Am. Chem. Soc., 50:2260 (1928). 0.089 g (0.26 mmol) of the sulfonamide in 5 ml MeOH was hydrogenated at 40 p.s.i. overnight using 6 mg of PtO₂ catalyst. Treatment of the crude product with HCl/ethyl acetate gave a yellow solid, 25 mg, which was triturated with ethyl ether (30% yield). ¹H NMR (CDCl₃): 7.45–7.40 (m, 2 H), 6.41–6.38 (m, 1 H), 4.51 (s, 1 H, SO₂NH), 4.38 (br s, 1 H, ring NH), 3.36–3.32 (m, 2 H, alkyl H's), 2.76 (t, J=6.2, 2 H, alkyl H's), 2.00 (s, 3 H, adamantyl H's), 1.94–1.89 (m, 2 H, alkyl H's), 1.83–1.80 (in, 6 H, adamantyl H's), 1.63–1.55 (m, 6 H, adamantyl H's).

EXAMPLE 38

3-(5-Acetoxy-2-naphthylsulfonyl)-3-azabicyclo[3.2.2]nonane

The title compound was prepared using a procedure similar to the procedure used to prepare Example 5. The 5-acetoxy-2-naphthalenesulfonyl chloride was prepared by acylating 0.30 g (1.25 mmol) of 5-hydroxy-2-naphthalenesulfonic acid with acetic anhydride and pyridine. The acetoxysulfonic acid was then treated with POCl₃ yielding an orange oil, 0.26 g. The oil was reacted with 0.12 g (0.96 mmol) of the azabicyclononane in CHCl₃ solution. The usual work-up gave 270 mg of a green oil. Purification by chromatotron using 8/1/1 hexane/acetone/chloroform gave a yellow oil, 75 mg (22% yield): ¹H NMR (CDCl₃): 8.34 (d, J=1.5, 1 H, H1), 7.99 (d, J=8.9, 1 H, H3), 7.87 (d, J=8.4, 1 H, H6), 7.78 (d, J=8.9, 1 H, H4), 7.60 (t, J=8.0, 1 H, H7), 7.40 (d, J=7.6, 1 H, H8), 3.29 (d, J=4.2, 4 H, N(CH₂R)₂), 2.50 (s, 3 H, CH₃), 2.08 (s, 2 H, N(CH₂CHR)₂) 1.74–1.61 (m, 8 H, alkyl H's).

EXAMPLE 39

3-(5-Hydroxy-2-naphthylsulfonyl)-3-azabicyclo[3.2.2]nonane

The title compound was prepared from 3-(5-Acetoxy-2-naphthylsulfonyl)-3-azabicyclo[3.2.2]nonane, by dissolving the acetoxy compound in 3 ml THF and then adding 2 ml water and 2 ml saturated sodium bicarbonate solution. After stirring overnight, the solvent was evaporated and the product extracted with chloroform. After drying over magnesium sulfate, the solvent was evaporated to give an orange oil. This was purified by chromatotron using 3/1 hexane/ethyl acetate which gave a yellow solid (32 mg, 48% yield): ¹H NMR (CDCl₃): 8.33 (d, J=8.8, 1 H, H3), 8.25 (d, J=1.6, 1 H, H1), 7.70 (d, J=8.8, 1 H, H4), 7.49 (d, J=8.3, 1 H, H6), 7.40 (t, J=7.8, 1 H, H7), 7.02 (d, J=7.4, 1 H, H8), 6.68 (br s, 1 H, OH), 3.30 (d, J=4.2, 4 H, N(CH₂R)₂), 2.08 (s, 2 H, N(CH₂CHR)₂),1.72–1.58 (in, 8 H, alkyl H's).

EXAMPLE 40

5-(6-Quinolinesulfonyl)-2-thia-5-azabicyclo[2.2.1]heptane

The title compound was prepared using a procedure similar to the procedure used to prepare Example 5. From 0.36 g (1.6 mmol) of the quinolinesulfonyl chloride and 0.31 g (2.0 mmol) of the thiaazabicycloheptane, there was obtained after work-up 0.42 g of an orange oil. Purification by chromatotron using 4/1 chloroform/ethyl acetate gave a yellow solid, 0.23 g (47% yield): mp 141.1°–143.2° C.; ¹H NMR (CDCl₃): 9.07 (d, J=4.2, 1 H, H2), 8.41 (d, J=1.9, 1 H, H5), 8.32 (d, J=8.4, 1 H, H3), 8.24 (d, J=8.9, 1 H, H7), 8.07 (d, J=8.9, 1 H, H8), 7.56 (d, J=8.3, 1 H, H4), 4.75 (s, I H, alkyl H), 3.70–3.65 (m, 1 H, alkyl H), 3.57–3.54 (m, 2 H, alkyl H's), 3.15–3.10 (m, 1 H, alkyl H), 3.01–2.95 (m, 1 H, alkyl H), 1.80–1.65 (m, 2 H, alkyl H's).

EXAMPLE 41

3-(1,2,3,4-Tetrahydro-6-quinolinesulfonyl)-3-azabicyclo[3.2.2]nonane

The title compound was prepared using a procedure similar to the procedure used to prepare the compound of Example 37. No purification was necessary to give a yellow solid (87% yield): mp 174°–181° C. (dec); ¹H NMR (CDCl₃): 7.77 (d, J=8.2, 1 H, aryl H), 7.67–7.63 (m, 2 H, aryl H's), 3.59 (t, J=5.5, 2 H, alkyl H's), 3.25 (d, J=4.2, 4 H, N(CH₂R)2), 2.98 (t, J=6.4, 2 H, alkyl H's), 2.33–2.25 (m, 2 H, alkyl H's), 2.10 (s, 2 H, N(CH₂CHR)₂), 1.78–1.63 (m, 8 H, alkyl H's).

EXAMPLE 42

3-(1-Acetyl-1,2,3,4-tetrahydro-6-quinolinesulfonyl)-3-azabicyclo[3.2.2]nonane The title compound was synthesized by addition of acetyl chloride to the compound of Example 41. 3-(1,2,3,4-Tetrahydro-6-quinolinesulfonyl)-3-azabicyclo-[3.2.2]nonane (100 mg, 0.31 mmol) was dissolved in dry tetrahydrofuran. The solution was cooled with an ice bath. Potassium tert-butoxide (76 mg, 0.68 mmol) was added, followed by acetyl chloride (0.03 ml, 0.41 mmol). The mixture was allowed to warm slowly to room temperature as it stirred overnight. The solvent was evaporated and the residue extracted with ethyl acetate. The organics were washed with brine, dried over magnesium sulfate and evaporated to give an orange solid. Purification by chromatotron using chloroform/ethyl acetate (9/1) gave a yellow solid (36 mg, 32% yield): mp 177°–179° C.; $^1$H NMR (CDCl$_3$): 7.56–7.52 (m, 3 H, aryl H's), 3.80 (t, J=6.3, 2 H, alkyl H's), 3.26 (d, J=4.2, 4 H, N(CH$_2$R)$_2$), 2.82, (t, J=6.6, 2 H, alkyl H's), 2.31 (s, 3 H, CH$_3$), 2.10–1.97 (m, 4 H, N(CH$_2$CHR)$_2$ and alkyl H's), 1.78–1.65 (m, 8 H, alkyl H's).

EXAMPLE 43

3-(4-Chloro-1-naphthylsulfonyl)-3-azabicyclo[3.2.2]nonane

The title compound was prepared by reacting 4-chloro-1-naphthalenesulfonyl chloride (0.27 g) with 3-azabicyclo[3.2.2]nonane (0.13 g) in the presence of DIEA using a procedure similar to that used in Example 5. Yield: 0.33 g, mp: 133.9°–137.3° C.

EXAMPLE 44

3-(4-Methoxy-1-naphthylsulfonyl)-3-azabicyclo[3.2.2]nonane

The title compound was prepared by reacting 4-methoxy-1-naphthalenesulfonyl chloride (0.25 g) with 3-azabicyclo[3.2.2]nonane (0.12 g) in the presence of DIEA (0.16 g) using a procedure similar to that used in Example 5. Yield: 0.24 g, mp 167.7°–169.5° C. (soften 166.1° C.).

EXAMPLE 45

4-(5-Chloro-1-naphthylsulfonyl)-4-azahomoadamantane

The title compound was prepared by reacting 5-chloro-1-naphthalenesulfonyl chloride (0.21 g) with 4-azahomoadamantane (0.18 g) in the presence of DIEA using a procedure similar to that used in Example 5. Yield: 0.25 g, mp: 118.3°–121.9° C.

EXAMPLE 46

N-(1-Acetoxy-3-naphthalenesulfonyl)-O-benzyl-4-hydroxyproline methyl ester

4-Acetoxy-2-naphthalenesulfonyl chloride (131 mg, 0.46 mmol) and O-benzyl-4-hydroxyproline methyl ester (108 mg, 0.46 mmol) were combined in CHCl$_3$ (20 ml) and pyridine (20 ml) and the mixture was stirred at room temperature for 15 hr. At this time the solvent was evaporated under reduced pressure and the residue was partitioned between EtOAc and 1N aq HCl. The EtOAc was then washed with saturated aq NaHCO$_3$, dried over Na$_2$SO$_4$, and concentrated. The residue was purified by flash chromatography using 1% acetone in CHCl$_3$ to provide 712 mg of the pure product as a white foam: $^1$H NMR (DMSO d$_6$) δ 2.16 (1H, m, ½ CH$_2$), 2.44 (1H, m, ½ CH$_2$), 2.49 (3H, s, CH$_3$CO), 3.64 (2H, m, CH$_2$N), 3.79 (3H, s, COOCH$_3$), 4.13 (1H, s, CH), 4.19 (2H, s, CH$_2$Ar), 4.48 (1H, t, J=4.91 Hz, CHN), 6.90 (2H, d, J=7.61 Hz, ArH), 7.05–7.21 (3H, m, ArH), 7.55–7.70 (2H, m, ArH), 7.75 (1H, s, ArH), 7.90 (1H, d, J=8.05 Hz, ArH), 7.97 (1H, d, J=7.62 Hz, ArH), 8.34 (1H, s, ArH).

EXAMPLE 47

4-(4-Methoxy-1-naphthylsulfonyl)-4-azahomoadamantane

The title compound was prepared by reacting 4-methoxy-1-naphthalenesulfonyl chloride (0.21 g) with 4-azahomoadamantane (0.20 g) in the presence of DIEA using a procedure similar to that of Example 5.

EXAMPLE 48

3-(4-Methoxy-1-naphthylsulfonyl)-3-azabicyclo[3.2.1]octane

The title compound was prepared by reacting 4-methoxy-1-naphthalenesulfonyl chloride (0.27 g) with 3-azabicyclo[3.2.2]nonane (0.16 g) in the presence of DIEA (0.30 g) using a procedure similar to that of Example 5. Yield: 0.34 g of a white solid, mp: 136.2°–138.6° C.

EXAMPLE 49

3-(4-Methyl-1-naphthylsulfonyl)-3-azabicyclo[3.2.2]nonane

The title compound was prepared by reacting 4-methyl-1-naphthalenesulfonyl chloride (0.69 g) with 3-azabicyclo[3.2.2]nonane (0.43 g) in the presence of DIEA using a procedure similar to that of Example 5. Yield 1.00 g of a grey solid, mp: 143.3°–147.2° C.

EXAMPLE 50

5-(1-Acetoxy-3-naphthylsulfonyl)-2-thia-5-azabicyclo-[2.2.1]heptane

4-Acetoxy-2-naphthalenesulfonyl chloride (375 mg, 2.50 mmol) and 2-thia-5-azabicyclo[2.2.1]heptane (711 mg, 2.50 mmol) were combined in CHCl$_3$ (20 ml) and pyridine (20 ml) and the mixture was stirred at room temperature for 15 hr. At this time the solvent was evaporated under reduced pressure and the residue was partitioned between EtOAc and 1N aq HCl. The EtOAc was then washed with saturated aq NaHCO$_3$, dried over Na$_2$SO$_4$, and concentrated. The residue was purified by flash chromatography using 3% acetone in CHCl$_3$ to provide of the pure product as a white foam (321 mg, 35% yield): $^1$H NMR (CDCl$_3$) δ 1.60–1.79 (2H, m, CH$_2$), 2.48 (3H, s, CH$_3$CO), 2.98 (1H, dd, J=7.78, 2.44 Hz, ½ CH$_2$), 3.18 (1H, d, J=10.21 Hz, ½ CH$_2$), 3.51 (2H, br m, CH$_2$), 3.67 (1H, d, J=9.48 Hz, CH), 4.70 (1H, s, CH), 7.61–7.70 (3H, m, ArH), 7.94–8.05 (m, 2H, ArH, 8.28 (s, 1H, ArH).

EXAMPLE 51

5-(1-Hydroxy-3-naphthylsulfonyl)-2-thia-5-azabicyclo-[2.2.1]heptane-2-dioxide

The product from Example 50 (202 mg, 0.56 mmol) was dissolved in MeOH (20 ml) and peracetic acid (228 mg, 720 mg of a 32% aqueous solution) was added. The resulting solution was stirred at room temperature for 5 hr. At this time the solvent was evaporated and the residue was partitioned between 1N HCl and CHCl$_3$. The CHCl$_3$ phase was dried (Na$_2$SO$_4$) and concentrated and the residue was purified by flash chromatography using 5% MeOH in CHCl$_3$ to provide the pure product as a white foam (112 mg, 57% yield): $^1$H NMR (DMSO d$_6$) δ 1.40 (1H, d, J=10.06 Hz, ½ CH$_2$), 2.15 (1H, d, J=11.47, ½ CH$_2$), 2.30 (1H, dd, J=13.16, 2.84, CH), 2.47 (2H, s, CH$_2$SO$_2$), 2.86 (1H, d, J=12.00 Hz, 1H, CHSO$_2$), 3.79 (1H, d, J=4.54 Hz, ½ CH$_2$N), 4.57 (1H, s, ½ CH$_2$N), 7.11 (1H, d, J=1.17 Hz, ArH), 7.64 (2H, m, ArH), 7.92 (1H, s, ArH), 8.07 (1H, m, ArH), 8.18 (1H, m, ArH), 8.28 (1H, s, ArH), 10.92 (1H, s, OH).

EXAMPLE 52

3-(1-Hydroxy-3-naphthylsulfonyl)-3-azabicyclo-[3.2.2]nonane

The product from Example 53 (637 mg, 1.70 mmol) was dissolved in MeOH (20 ml) and KOH (150 mg) in water (3 ml) was added and the mixture was maintained for 1 hr. At this time the solvent was evaporated under reduced pressure and the residue was partitioned between CHCl$_3$ and 1N aq HCl. The CHCl$_3$ phase was dried over Na$_2$SO$_4$ then concentrated. The residue was purified by flash chromatography using 5% acetone in CHCl$_3$. The pure product was obtained as a pink foam (412 mg, 73% yield): $^1$H NMR (CDCl$_3$) δ 1.53–1.89 (8H, m, 4×CH$_2$), 2.02 (2H, br s, 2×CH), 3.28 (4H, d, J=4.16 Hz, 2×CH$_2$), 7.31 (1H, s, ArH), 7.58–7.68 (2H, m, ArH), 7.85–7.98 (2H, m, ArH), 8.27–8.36 (1H, m, ArH).

EXAMPLE 53

3-(1-Acetoxy-3-naphthylsulfonyl)-3-azabicyclo [3.2.2]nonane

4-Acetoxy-2-naphthalenesulfonyl chloride (861 mg, 3.02 mmol) and 3-azabicyclo[3.2.2]nonane (379 mg, 3.02 mmol) were combined in CHCl$_3$ (20 ml) and pyridine (20 ml) and the mixture was stirred at room temperature for 15 hr. At this time the solvent was evaporated under reduced pressure and the residue was partitioned between EtOAc and 1N aq HCl. The EtOAc was then washed with saturated aq NaHCO$_3$, dried over Na$_2$SO$_4$, and concentrated. The residue was purified by flash chromatography using 1% acetone in CHCl$_3$ to provide the pure product as a white foam (712 mg, 63% yield): $^1$H NMR (CDCl$_3$) δ 1.52–1.84 (8H, m, 4×CH$_2$), 2.02–2.13 (2H, br s, 2×CH), 2.46 (3H, s, CH$_3$CO), 3.31 (4H, d, J=4.2 Hz, 2×CH$_2$), 7.56–7.71 (3H, m, ArH), 7.92–8.02 (2H, m, ArH).

EXAMPLE 54

3-[1-(3-Pyridinylmethoxy)-3-naphthylsulfonyl]-3-azabicyclo[3.2.2]nonane

The product from Example 52 (147 mg, 0.44 mmol), 3-picolylchloride hydrochloride (73 mg, 0.44 mmol and a crystal of KI were combined in DMF (30 ml). Sodium hydride (44 mg, 1.1 mmol, a 60% dispersion in oil) was added and the mixture was stirred at 90° C. for 15 hr. At this time the solvent was evaporated under reduced pressure and the residue was partitioned between 1N aq KOH and CHCl$_3$. The CHCl$_3$ phase was dried (Na$_2$SO$_4$) and concentrated and the residue was purified by flash chromatography using 5% acetone in CHCl$_3$. The pure product was obtained as a tan foam (124 mg, 66% yield): $^1$H NMR (CDCl$_3$) δ 1.53–1.76 (8H, m, 4×CH$_2$), 2.06 (2H, s, 2×CH), 3.21 (4H, d, J=4.19 Hz, 2×CH$_2$), 5.34 (2H, s, CH$_2$Ar), 7.12 (1H, s, ArH), 7.37 (1H, m, ArH), 7.64 (2H, m, ArH), 7.82–7.98 (3H, m, ArH), 8.35 (1H, m, ArH), 8.62 (1H, m, ArH), 8.80 (1H, m, ArH).

EXAMPLE 55

4-[1-(3-Pyridinylmethoxy)-3-naphthylsulfonyl]-4-azahomoadamantane

The product from Example 61 (77 mg, 0.21 mmol), 3-picolylchloride hydrochloride (42 mg, 0.21 mmol) and a crystal of KI were combined in DMF (30 ml). Sodium hydride (41 mg, 1.1 mmol, a 60% dispersion in oil) was added and the mixture was stirred at 90° C. for 15 hr. At this time the solvent was evaporated under reduced pressure and the residue was partitioned between 1N aq KOH and CHCl$_3$. The CHCl$_3$ phase was dried (Na$_2$SO$_4$) and concentrated and the residue was purified by flash chromatography using 5% acetone in CHCl$_3$. The pure product was obtained as a tan foam (52 mg, 54% yield): $^1$H NMR (CDCl$_3$) δ 1.25–1.59 (7H, m, alkyl), 1.65–1.98 (8H, m, alkyl), 2.21 (1H, s, CH), 3.45 (2H, d, J=3.74 Hz, CH$_2$), 4.48 (1H, br m, CH), 7.20 (1H, d, J=1.37 Hz, ArH), 7.39 (1H, m, ArH), 7.64 (2H, m, ArH), 7.85–7.89 (m, 3H, ArH), 8.01 (1H, s, ArH), 8.30–8.39 (1H, m, ArH), 8.65 (1H, dd, J=6.21, 1.35 Hz, ArH), 8.82 (1H, s, ArH).

EXAMPLE 56

3-(1-Carboxlmethoxy-3-naphthylsulfonyl)-3-azabicyclo[3.2.2]nonane

The product from Example 52 (117 mg, 0.35 mmol), bromomethylacetate (54 mg, 0.35 mmol) and a crystal of KI were combined in DMF (30 ml). Sodium hydride (44 mg, 1.1 mmol, a 60% dispersion in oil) was added and the mixture was stirred at 90° C. for 15 hr. At this time the solvent was evaporated under reduced pressure and the residue was partitioned between EtOAc and 1N HCl. The EtOAc phase was dried (Na$_2$SO$_4$) and concentrated and the residue was purified by flash chromatography using 30% EtOAc in hexane. The pure product was obtained as a white foam, 51 mg (86% yield): $^1$H NMR (CDCl$_3$) δ 1.52–1.81 (8H, m, 4×CH$_2$), 2.06 (2H, br s, 2×CH), 3.34 (4H, 2×CH$_2$), 3.83 (3H, s, COOCH$_3$), 4.94 (2H, s, OCH$_2$), 6.98 (1H, s, ArH), 7.61 (m, 2H, ArH), 7.94 (m, 2H, ArH), 8.82 (1H, d, J=5.7 Hz, ArH). This material (62 mg, 0.15 mmol) was dissolved in MeOH (10 mL) and KOH (50 mg) in H$_2$O (2 mL) was added. The mixture was stirred 3 hr then the solvent was evaporated and the residue was partitioned between 1N HCl and CHCl$_3$. The CHCl$_3$ phase was dried (Na$_2$SO$_4$) and concentrated. The residue was purified by flash chromatography using 10% MeOH in CHCl$_3$ to provide the pure product (51 mg, 86%) as a white foam: $^1$H NMR (CDCl$_3$) δ 1.21–1.68 (8H, m, 4×CH$_2$), 1.71–1.94 (2H, br s, 2×CH$_2$), 3.31 (4H, m, 2×CH$_2$), 4.52 (2H, br s, OCH$_2$), 6.99 (1H, s, ArH), 7.24 (2H, m, ArH), 7.61 (2H, m, ArH), 8.14 (1H, br s, ArH).

EXAMPLE 57

3-[1-[1-(3-Piperazinylpropoxy)-3-naphthylsulfonyl]] -3-azabicyclo[3.2.2]nonane

The product from Example 58 (92 mg, 0.16 mmol) was dissolved in MeOH (30 ml) and a solution of anhydrous HCl in MeOH (5 ml) was added. The solution was stirred at room temperature for 3 hr. At this time the solvent was evaporated under reduced pressure to provide an HCl salt as a white foam (87 mg, 100% yield): $^1$H NMR (CDCl$_3$) δ 1.51–1.85 (8H, m, 4×CH$_2$), 2.12 (2H, br s, 2×CH), 2.47 (2H, br m, CH$_2$), 2.60 (2H, br s, CH$_2$N), 3.25–3.72 (8H, br s, 4×CH$_2$), 4.48 (2H, br s, CH$_2$O), 7.12 (s, 1H, ArH), 7.77 (2H, m, ArH), 8.05 (1H, s, ArH), 8.22 (1H, m, ArH), 8.38 (1H, m, ArH), 9.98 (2H, br s, NH$_2$).

EXAMPLE 58

3[1-[1-(3-t-Butoxycarbonylpiperazinylpropoxy)-3-naphthylsulfonyl]]-3-azabicyclo[3.2.2]nonane The compound from Example 52 (200 mg, 0.60 mmol), 1-(3-chloropropyl)piperazine dihydrochloride monohydrate (158 mg, 0.60 mmol) and a crystal of KI were combined in DMF (30 ml). Sodium hydride (35 mg, 0.9 mmol, a 60% dispersion in oil) was added and the mixture was stirred at 90° C. for 15 hr. At this time the solvent was evaporated under reduced pressure and the residue was partitioned between EtOAc and 1N HCl. The EtOAc phase was washed with sat aq $NaHCO_3$ then dried ($Na_2SO_4$) and concentrated. The residue was purified by flash chromatography using 2% MeOH in $CHCl_3$ to provide a white foam (212 mg, 63% yield): $^1H$ NMR ($CDCl_3$) δ 1.46 (9H, s, t-Bu), 1.47–1.58 (8H, m, 4×$CH_2$), 2.0–2.15 (2H, br s, 2×CH), 2.45 (2H, m, $CH_2$), 2.48 (4H, br s, 2×$CH_2$), 2.65 (2H, t, J=7.02 Hz, $CH_2N$), 3.33 (4H, d, J=4.19 Hz, 2×$CH_2$), 3.47 (2H, t, J=4.24 Hz, $CH_2O$), 7.05 (1H, s, ArH), 7.27 (1H, s, ArH), 7.58–7.73 (2H, m, ArH), 7.85–7.92 (2H, m, ArH), 8.26–8.35 (1H, m, ArH).

EXAMPLE 59

3-[1-[1-(3-Dimethylamino)-3-naphthylsulfonyl]]-3-azabicyclo[3.2.2]nonane

The compound from Example 52 (117 mg, 0.35 mmol), 1-(3-dimethylaminoethyl chloride hydrochloride (51 mg, 0.35 mmol) and a crystal of KI were combined in DMF (30 ml). Sodium hydride (21 mg, a 60% dispersion in oil) was added and the mixture was stirred at 90° C. for 15 hr. At this time the solvent was evaporated under reduced pressure and the residue was partitioned between $CHCl_3$ and 1N KOH. The $CHCl_3$ phase was dried ($Na_2SO_4$) and concentrated. The residue was purified by flash chromatography using 8% MeOH in $CHCl_3$ to provide a white foam (84 mg, 59% yield): $^1H$ NMR ($CDCl_3$) δ 1.42–1.80 (8H, m, 4×$CH_2$), 2.14 (2H, s, 2×CH), 2.45 (6H, s, 2×$CH_3N$), 2.96 (2H, t, J=5.53 Hz, $CH_2$), 3.30 (4H, d, J=4.2 Hz, 2×$CH_2N$), 4.32 (2H, t, J=5.56 Hz, $CH_2$), 7.06 (1H, s, ArH), 7.51–7.63 (2H, m, ArH), 7.85–7.94 (2H, m, ArH), 8.28 (1H, d, J=8.95 Hz, ArH).

EXAMPLE 60

4-(1-Acetoxy-3-naphthylsulfonyl)-4-azahomoadamantane

4-Acetoxy-2-naphthalenesulfonyl chloride (480 mg, 1.69 mmol) and 4-azahomoadamantane (255 mg, 1.69 mmol) were combined in $CHCl_3$ (20 ml) and pyridine (20 ml) and the mixture was stirred at room temperature for 15 hr. At this time the solvent was evaporated under reduced pressure and the residue was partitioned between EtOAc and 1N aq HCl. The EtOAc was then washed with saturated aq $NaHCO_3$, dried over $Na_2SO_4$, and concentrated. The residue was purified by flash chromatography using 3% acetone in $CHCl_3$ to provide the pure product as a white foam (273 mg, 67% yield): $^1H$ NMR ($CDCl_3$) δ 1.46–1.58 (7H, m, alkyl), 1.73–1.98 (8H, m, alkyl), 2.23 (1H, br m, 1H), 2.50 (3H, s, $CH_3CO$), 3.52 (2H, d, 3.63 Hz, $CH_2$), 4.51 (1H, br m, CH), 7.60–7.72 (3H, m, ArH), 7.89–8.01 (2H, m, ArH), 8.27 (1H, s, ArH).

EXAMPLE 61

4-(1-Hydroxy-3-naphthylsulfonyl)-4-azahomoadamantane

The product from Example 60 (161 mg, 0.40 mmol) was dissolved in MeOH (20 ml) and KOH (113 mg) in water (3 ml) was added and the mixture was maintained for 1 hr. At this time the solvent was evaporated under reduced pressure and the residue was partitioned between $CHCl_3$ and 1N aq HCl. The $CHCl_3$ phase was dried over $Na_2SO_4$ then concentrated. The residue was purified by flash chromatography using 5% acetone in $CHCl_3$. The pure product was obtained as a pink foam (98 mg, 68% yield): $^1H$ NMR ($CDCl_3$) δ 1.23–1.62 (7H, m, alkyl), 1.64–1.98 (8H, m, alkyl), 2.21 (1H, br s, CH), 3.54 (2H, d, J=3.63 Hz, $CH_2$), 4.49 (1H, br m, CH), 7.25–7.38 (1H br s, OH), 7.38 (1H, d, J=1.29 Hz, ArH), 7.51–7.70 (2H, m, ArH), 7.86–8.01 (2H, m, ArH), 8.25–8.38 (1H, m, ArH).

EXAMPLE 62

5-(1-Hydroxy-3-naphthylsulfonyl)-2-thia-5-azabicyclo-[2.2.1]heptane

The compound of from Example 50 (207 mg, 0.57 mmol) was dissolved in MeOH (20 ml) and KOH (160 mg) in water (3 ml) was added and the mixture was maintained for 1 hr. At this time the solvent was evaporated under reduced pressure and the residue was partitioned between $CHCl_3$ and 1N aq HCl. The $CHCl_3$ phase was dried over $Na_2SO_4$ then concentrated. The residue was purified by flash chromatography using 5% acetone in $CHCl_3$. The pure product was obtained as a white foam (173 mg, 92% yield): $^1H$ NMR (DMSO $d_6$) δ 1.35 (1H, d, J=10.57, ½ $CH_2$), 1.57 (1H, d, J=10.48, ½ $CH_2$), 2.83–3.02 (2H, m, $CH_2$), 3.24–3.51 (2H, m, $CH_2$), 3.61 (1H, s, CH), 4.58 (1H, s, CH), 7.14 (1H, s, ArH), 7.61 (2H, m, ArH), 7.90 (1H, s, ArH), 8.06 (1H, m, ArH), 8.17 (1H, m, ArH), 10.87 (1H, br s, OH).

EXAMPLE 63

5-[1-(3-Pyridinylmethoxy)-3-naphthylsulfonyl]-2-thia-5-azabicyclo[2.2.1]-heptane The product from Example 62 (66 mg, 0.20 mmol), 3-picolylchloride hydrochloride (40 mg, 0.20 mmol and a crystal of KI were combined in DMF (30 ml). Sodium hydride (41 mg, 1.1 mmol, a 60% dispersion in oil) was added and the mixture was stirred at 90° C. for 15 hr. At this time the solvent was evaporated under reduced pressure and the residue was partitioned between 1N aq KOH and $CHCl_3$. The $CHCl_3$ phase was dried ($Na_2SO_4$) and concentrated and the residue was purified by flash chromatography using 5% acetone in $CHCl_3$. The pure product was obtained as a tan foam (49 mg, 58% yield): $^1H$ NMR ($CDCl_3$) δ 1.52 (1H, d, J=10.57 Hz, ½ $CH_2$), 1.69 (1H, J=10.74 Hz, ½ $CH_2$), 1.81 (1H, br s, CH), 2.91 (1H, dd, J=10.12, 2.53, ½ $CH_2$), 3.09 (1H, d, J=10.15 Hz, ½ $CH_2$), 3.50 (2H, m, $CH_2$), 3.61 (1H, dd, J=10.21, 1.14 Hz, CH), 4.62 (2H, s, $CH_2Ar$), 7.19 (1H, d, J=1.39 Hz, ArH), 7.39 (1H, dd, J=11.61, 4.87 Hz, 7.60–7.69 (2H, m, ArH), 7.82–7.98 (2H, m, ArH), 8.01 (1H, s, ArH), 8.30–8.38 (1H, m, ArH), 8.68 (1H, dd, J=10.19, 1.35 Hz, ArH), 8.81 (1H, d, J=1.86 Hz, ArH).

Part III: Pharmacology and Biological Assays

In order to establish the pharmacological properties of the compounds of formula (I) as a method of treatment for immuno-inflammatory disease in a patient suffering therefrom—such diseases being for the most part, but not limited exclusively to, graft rejection, ischemia reperfusion, asthma/allergy, delayed type hypersensitivity and AIDS—an in vitro assay was used to determine the effect of the compounds of the present invention on $β_2$ mediated adhesion. Because human endothelial cells (EC's) express low levels of ICAM-1 on their surface and stimulation with TNF-α increases its expression, adhesion of lymphocytes can be measured following the principal assay design as described below for the human B cell line JY.

A. Cell Adhesion to Stimulated Endothelial Cells

Human umbilical vein endothelial cells (HUVEC) were purchased from Clonetics (San Diego, Calif.) at passage number 2. The cells were growth on 0.5% porcine skin gelatin pre-coated flasks (Sigma, St. Louis, Mo.) in EGM-UV media (Clonetics, San Diego, Calif.) supplemented with 10% fetal bovine serum. Cells are re-fed every 2–3 days, reaching confluence by day 4 to 6. The cells are monitored for factor VIII antigen and our results show that at passage 12, the cells are positive for this antigen. The endothelial cells are not used following passage 7. Endothelial cells are grown to confluency in 96-well micro-titer assay plate.

The human B cell line JY was cultured in RPMI media containing 10% fetal calf serum at 37° C. in a humidified $CO_2$ atmosphere. JY cells are loaded with the fluorescent dye indicator BCECF as follows: JY cells are washed twice with HBSS and cells are then re-suspended in HBSS at $5\times10^6$ cells/ml; BCECF-AM (Molecular Probes), stock concentration=1 mg/ml in DMSO, is added to the JY cells to a final concentration of 2 µg/ml; cells are incubated in the dark at 37° C. for 30–45 minutes; washed twice with HBSS and used in the assay.

The compounds presented in this invention are typically dissolved in 2.5 mg HSA/ml DME at four times the assay concentration and pH adjusted with 7.5% Na bicarbonate as needed. A confluent monolayer of human EC's in microtiter plates is stimulated with 50 U/ml TNF-α for 20 hours, and on the next day washed twice with DMEM-HSA before use. The EC's may be fixed by treatment with 3% paraformaldehyde. The assay plate is placed on ice, and test compound is added to quadruplicate wells, then all wells received $2.5\times10^5$ labeled JY cells and an optional stimulus (e.g. phorbol ester). Plates are incubated for 30 minutes at 37° C. in a $CO_2$ incubator. Plates are washed four times with 100 µl PBS/well and the fluorescence of the adherent cells is measured using a fluorescence reader. Fluorescence in each well is measured as Arbitrary Fluorescence Units and percent adhesion in the absence of peptide is adjusted to 100% and the percent adhesion in the presence of peptides is calculated. Inhibitory concentrations ($IC_{50}$) are determined based on 100% adhesion of cells that were incubated in the absence of drugs. Stimulation of protein kinase C by phorbol esters such as 13,14-phorbol myristate acetate (PMA) increases the observed adhesion approximately 5-fold. This PMA induced adhesion is 100% blocked by anti-LFA-1 or anti-CD18 antibodies and about 75–80% by anti-ICAM-1 antibodies, while it is unaffected by antibodies to Mac-1, $\alpha_4$ or control antibodies. Thus, this assay measures preferentially the interaction between ICAM-1 and LFA-1.

The effect of the compounds of the present invention on $\beta_2$ mediated adhesion can also be measured using purified recombinant ICAM-1 as an adhesion substrate. Adhesion of BCECF-AM labelled JY cells to ICAM-1 pre-coated 96-well assay plates is performed as described for adhesion to endothelial cells. Assay plates are coated with purified ICAM-1 for 24 hours at 4C and washed three times with HBSS before use.

Test results for certain exemplary compounds of the present invention are given in Table 1.

B. Evaluation of Cytotoxicity In Vitro

Cytotoxicity of the most active compounds was evaluated in vitro by measuring uptake of propidium iodine or in an ALAMAR BLUE assay according to the manufacturer's specifications (Alamar Biosciences, Inc., 4110 N. Freeway Blvd., Sacramento, Calif. 95834). The activity in the assay was not due to cytotoxic activity of the compounds. The compounds of Examples 3 and 5 did not inhibit the proliferation of JY cells or U937 cells at concentrations where they were active in the adhesion assay measured after 20 hours.

TABLE 1

Part IV
Biological Activity of Selected Sulfonamides

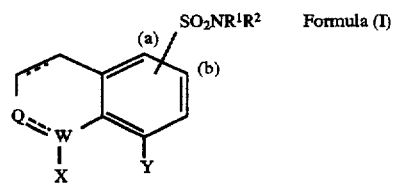

Formula (I)

| EXAMPLE NO. | Q | W | X | Y | $-SO_2-$ RING POSITION | $-NR^1R^2$ | JY-EC[1] $IC_{50}$ µM[2] |
|---|---|---|---|---|---|---|---|
| 3 | C | C | Cl | H | (b) | —NH(1-adamantyl) | 3 |
| 5 | C | C | Cl | H | (b) | 3-azabicyclo-[3.2.2]nonane | 0.5 |
| 15 | C | C | acetoxy | H | (b) | —NH(1-adamantyl) | 56 |
| 17 | C | C | Cl | H | (b) | 3-azabicyclo-[3.2.1]octane | 15 |
| 18 | C | C | Cl | H | (b) | 4-azahomoadamantane | 0.25 |
| 20 | C | C | Cl | H | (b) | 2-thia-5-aza-bicyclo[2.2.1]-heptane | 6 |
| 21 | C | C | Cl | H | (b) | 2-oxa-5-aza-bicyclo[2.2.1]-heptane | 86 |
| 24 | C | C | Cl | H | (b) | —NH(3-adamantane-carboxylic acid- | 136 |

TABLE 1-continued

Part IV
Biological Activity of Selected Sulfonamides

Formula (I)

| EXAMPLE NO. | Q | W | X | Y | $-SO_2-$ RING POSITION | $-NR^1R^2$ | JY-EC[1] $IC_{50}$ µM[2] |
|---|---|---|---|---|---|---|---|
| 29 | C | N | H | H | (b) | 3-azabicyclo-[3.2.2]nonane 1-yl) | 8 |
| 30 | C | N | H | H | (b) | $-NH$(1-adamantyl) | 23 |
| 31 | C | N | H | H | (b) | 4-azahomoadamantane | 5 |
| 32 | C | N | H | H | (b) | $-NH$(2-adamantyl) | 234 |
| 35 | C | C | $-NH_2$ | H | (b) | 3-azabicyclo-[3.2.2]nonane | 13.6 |
| 44 | C | C | H | MeO | (a) | 3-azabicyclo-[3.2.2]nonane | 1.6 |
| 54 | C | C | H | 3-pyridinyl-methoxy | (b) | 3-azabicyclo-[3.2.2]nonane | 4.4 |
| 55 | C | C | H | 3-pyridinyl-methoxy | (b) | 4-azahomoadamantane | 2.1 |

*1,2,3,4-tetrahydroquinoline
[1]See body of patent for detailed description of method.
[2]$IC_{50}$: Concentration at which adhesion is inhibited to 50% of control level.

Part V: Pharmaceutical Compositions

As indicated previously, the inventive compounds of formula I can be formulated into pharmaceutical compositions. In determining when a compound of formula I is indicated for the treatment of a given disease, the particular disease in question, its severity, as well as the age, sex, weight, and condition of the subject to be treated, must be taken into consideration and this perusal is to be determined by the skill of the attendant physician.

For medical use, the amount required of a compound of Formula I, thereof to achieve a therapeutic effect will, of course, vary both with the particular compound, the route of administration, the patient under treatment, and the particular disorder or disease being treated. A suitable dose of a compound of Formula I, or a pharmacologically acceptable salt thereof for a mammalian patient suffering from, or likely to suffer from any condition as described hereinbefore is 0.1 µg to 500 mg of the compound of formula I, per kilogram body weight of the mammalian patient. In the case of systematic administration, the dose may be in the range of 0.5 to 500 mg of the compound per kilogram body weight, the most preferred dosage being 0.5 to 50 mg/kg of mammal body weight administered two to three times daily. In the case of topical administration, e.g., to the skin or eye, a suitable dose may be in the range of 0.1 µg to 100 µg of the compound per kilogram, typically about 0.1 µg/kg.

In the case of oral dosing, a suitable dose of a compound of Formula I, or a physiologically acceptable salt thereof, may be as specified in the preceding paragraph, but most preferably is from 1 mg to 10 mg of the compound per kilogram, the most preferred dosage being from 1 mg to 5 mg/kg of mammal body weight, for example, from 1 to 2 mg/kg. Most preferably, a unit dosage of an orally administrable composition encompassed by the present invention contains less than about 1.0 g of a formula I compound.

It is understood that the ordinarily skilled physician or veterinarian will readily determine and prescribe the effective amount of a compound of Formula I to prevent or arrest the progress of the condition for which treatment is administered. In so proceeding, the physician or veterinarian could employ relatively low doses at first, subsequently increasing the dose until a maximum response is obtained.

While it is possible for an active ingredient to be administered alone, it is preferable to present it as a pharmaceutical formulation comprising a compound of Formula I and a pharmaceutically acceptable carrier therefor. Such formulations constitute a further feature of the present invention.

The formulations, both for human and veterinary medical use, of the present invention comprise an active ingredient of Formula I, in association with a pharmaceutically acceptable carrier therefor and optionally other therapeutic ingredient(s), which are generally known to be effective in treating the disease or condition encountered. The carrier(s) must be "acceptable" in the sense of being compatible with the other ingredients of the formulations and not deleterious to the recipient thereof.

The formulations include those in a form suitable for oral, pulmonary, ophthalmic, rectal, parenteral (including subcutaneous, intramuscular, and intravenous), intra-articular, topical, nasal, inhalation (e.g., with an aerosol) or buccal administration. Such formulation are understood to include long-acting formulations known in the art.

The formulations may conveniently be presented in unit dosage form and may be prepared by any of the methods well known in the art of pharmacy. All methods may include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desire formulation.

The compounds of formula I are preferably administered orally, when administered to a patient in need thereof. Formulations of the present invention suitable for oral administration may be in the form of discrete units such as capsules, cachets, tablets, or lozenges, each containing a predetermined amount of the active ingredient in the form of a powder or granules; in the form of a solution or suspension in an aqueous liquid. Formulations for other uses could involve a nonaqueous liquid; in the form of an oil-in-water emulsion or a water-in-oil emulsion; in the form of an aerosol; or in the form of a cream or ointment or impregnated into a transdermal patch for use in administering the active ingredient transdermally, to a patient in need thereof. The active ingredient of the present inventive compositions may also be administered to a patient in need thereof in the form of a bolus, electuary, or paste.

Each of the publications and patent documents referred to herein, is incorporated herein by reference in its entirety.

What is claimed is:

1. A sulfonamide Compound encompassed by the following Formula (I),

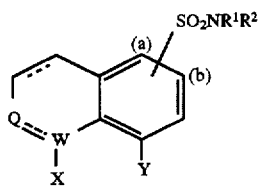

Formula (I)

wherein,

W and Q are selected from a carbon and a nitrogen atom, provided that W and Q are not both simultaneously nitrogen atoms;

X and Y may be the same or different and are selected from a hydrogen atom, a halogen atom, a methyl group, an acetyl group, —$OR^3$, $NH_2$, —$NHR^4$ and —$NR^5R^6$;

(a) and (b) denote ring positions which may be substituted with the sulfonyl moiety (—$SO_2$—);

dotted lines denote double bonds which are optional;

$R^1$ and $R^2$ may be the same or different and are selected from a hydrogen atom, $C_{1-8}$ alkyl, $C_{2-8}$ alkenyl, $C_{3-9}$ cycloalkyl, aminopropyl, phenyl, 1-adamantyl, 2-adamantyl, bornyl, 1-adamantanemethyl, 3-noradamantyl, 3-aminoquinuclidine, 3-adamantane carboxylic acid-1-yl, 2-oxaadamantane-1-yl, 1-azaadamantane-4-yl and 1-hydroxy-3-adamantyl, 1-hydroxy-2-azahomoadamantane-6-yl, or alternatively, $R^1$ and $R^2$ together with the nitrogen atom to which they are attached form a bridged polycyclic moiety selected from the group consisting of 3-azabicyclo-[3.3.2]decane, 3-azabicyclo[3.2.2]nonane, 3-azabicyclo-[3.2.1]octane, 4-azahomoadamantane, 2-azaadamantane, 2-thia-5-azabicyclo[2.2.1]heptane, 2-oxo-5-azabicyclo-[2.2.1]heptane, 2,5-diazabicyclo[2.2.1]heptane, 5-methylformyl-2,5-diazabicyclo[2.2.1]heptane, 1-hydroxy-4-azahomoadamantane, 3-aminoquinuclidine and 3-thia-5-azabicyclo[2.2.1]heptane-2,2 dioxide, or alternatively, $R^1$ and $R^2$ together with the nitrogen atom to which they are attached form a monocyclic moiety selected from the group consisting of 4-benzyloxy-2-pyrrolidine carboxylic acid and 4-benzyloxy-2-methyl-oxycarbonyl pyrrolidine;

$R^3$ to $R^6$ may be the same or different and are selected from a hydrogen atom, $C_{1-8}$ alkyl, $C_{3-9}$ cycloalkyl, acetyl, fluroenylmethyloxycarbonyl, pyridylmethyl, carobymethyl, piperazinylpropyl, (tert-butoxycarbonyl piperzinyl)propyl and dimethylaminoethyl; or a pharmaceutically acceptable salt thereof;

provided that 3-(2-naphthylsulfonyl)-3-azabicyclo[3.2.2] nonane is excluded from formula (I).

2. The sulfonamide compound of claim 1, wherein Q is a carbon atom and W is a nitrogen atom.

3. The sulfonamide compound of claim 1, wherein Q is a nitrogen atom and W is a carbon atom.

4. The sulfonamide compound of claim 1, wherein Q and W are each carbon atoms.

5. The sulfonamide compound of claim 1, wherein Q and W are each carbon atoms, X is a chlorine atom, Y is a hydrogen atom, $R^1$ is an adamantyl group and $R^2$ is a hydrogen atom.

6. The sulfonamide compound of claim 1, wherein Q and W are each carbon atoms, X is a chlorine atom, Y is a hydrogen atom, and $R^1$ and $R^2$ and the nitrogen atom to which they are mutually bonded form a bridged polycyclic moiety selected from the group consisting of 4-azahomoadamantane and 3-azabicyclo[3.2.2]nonane.

7. The sulfonamide compound of claim 1, wherein Q and W are each carbon atoms, X is a hydrogen atom, Y is a 3-pyridinylmethoxy group, and $R^1$ and $R^2$ and the nitrogen atom to which they are mutually bonded form a bridged polycyclic moiety selected from the group consisting of 4-azahomoadamantane and 3-azabicyclo-[3.2.2]nonane.

8. The sulfonamide compound of claim 1, wherein said compound is a 5-chloro-2-naphthalenesulfonamide derivative encompassed by formula (I).

9. The sulfonamide compound of claim 1, wherein said compound of formula (I) is

N-(1-adamantyl)-5-chloro-2-naphthalenesulfonamide, 4-(5-chloro-2-naphthylsulfonyl)-4-azahomoadamantane, 3-(5-chloro-2-naphthylsulfonyl)-3-azabicyclo[3.2.2] nonane, 4-[4-(3-pyridinylmethoxy)-2-naphthylsulfonyl)-4-azahomoadamantane, 3-(4-(3-pyridinylmethoxy)-2-naphthylsulfonyl)-3-azabicyclo[3.2.2]nonane, 3-(1-acetoxy-3-naphthylsulfonyl)-3-azabicyclo-[3.2.2] nonane, 3-(1-hydroxy-3-naphthylsulfonyl)-3-azabicyclo-3.2.2 ]nonane, 3-[1-[1-(3-dimethylamino)-3-naphthylsulfonyl]]-3-azabicyclo[3.2.2]nonane, 4-(1-hydroxy-3-naphthylsulfonyl)-4-azahomoadamantane, 4-(1-acetoxy-3-naphthylsulfonyl)-4-azahomoadamantane, 4-(4-methoxy-1-naphthylsulfonyl)-4-azahomoadamantane, 3-(4-methoxy-1-naphthylsulfonyl)-3-azabicyclo-[3.2.2] nonane, 3-(4-chloro-1-naphthylsulfonyl)-3azabicyclo-[3.2.2] nonane, 3-(1,2,3,4-tetrahydro-6-quinolinesulfonyl)-3-azabicyclo [3.2.2]nonane, 3-(5-acetoxy-2-naphthylsulfonyl)-3-azabicyclo-[3.2.2] nonane, 6-(5-chloro-2-naphthylsulfonyl)-6-amino-1-hydroxy-2-azahomoadamantane, 4-(6-quinolinesulfonyl)-4-azahomoadamantane, 1-(6-quinolinesulfonyl)-1-azahomoadamantane, 3-(6-quinolinesulfonyl)-3-azabicyclo[3.2.2]nonane, 3-(5-chloro-2-naphthylsulfonyl)-3-aminonoradamantane, 2-(5-chloro-2-naphthylsulfonyl)-2-aminoadamantane, 2-(5-chloro-2-naphthylsulfonyl)-2-(3-aminopropyl)-2-aminoadamantane, 1-(5-chloro-2-naphthylsulfonyl)-1-phenyl-1,3-diaminopropane, 1-(2-naphthylsulfonyl)-1-aminoadamantane, 3-(5-chloro-2-naphthylsulfonyl)-3-azabicyclo-[3.2.1]octane, 5-(5-chloro-2-naphthylsulfonyl)-2-thia-5-azabicyclo [2.2.1]heptane, 4-(2-naphthylsulfonyl)-4-azahomoadamantane, 3-(1-methoxy-4-naphthylsulfonyl)-3-azabicyclo-[3.2.2] nonane, 3-(5-amino-2-naphthylsulfonyl)-3-azabicyclo-[3.2.2] nonane, or said pharmaceutically acceptable salt thereof.

10. A method of treating an immuno-inflammatory disease in a mammalian patient in need of said treatment, the method comprising the step of administering to the mammalian patient a pharmaceutically effective amount of a sulfonamide Compound according to claim 1.

11. The treatment method of claim 10, wherein Q is a carbon atom and W is a nitrogen atom.

12. The treatment method of claim 10, wherein Q is a nitrogen atom and W is a carbon atom.

13. The treatment method of claim 10, wherein Q and W are each carbon atoms.

14. The treatment method of claim 10, wherein Q and W are each carbon atoms, X is a chlorine atom, Y is a hydrogen atom, $R^1$ is an adamantyl group and $R^2$ is a hydrogen atom.

15. The treatment method of claim 10, wherein Q and W are each carbon atoms, X is a chlorine atom, Y is a hydrogen atom, and $R^1$ and $R^2$ and the nitrogen atom to which they are mutually bonded form a polycyclic moiety selected from the group consisting of 4-azahomoadamantane and 3-azabicyclo [3.2.2]nonane.

16. The treatment method of claim 10, wherein Q and W are each carbon atoms, X is a hydrogen atom, Y is a 3-pyridinylmethoxy group, and $R^1$ and $R^2$ and the nitrogen atom to which they are mutually bonded form a bridged polycyclic moiety selected from the group consisting of 4-azahomoadamantane and 3-azabicyclo[3.2.2]nonane.

17. The treatment method of claim 10, wherein said compound is a 5-Chloro-2-naphthalenesulfonamide derivative encompassed by formula (I).

18. The treatment method of claim 10, wherein said compound of formula (I) is

N-(1-adamantyl)-5-chloro-2-naphthalenesulfonamide, 4-(5-chloro-2-naphthylsulfonyl)-4-azahomoadamantane, 3-(5-chloro-2-naphthylsulfonyl)-3-azabicyclo-[3.2.2] nonane, 4-[4-(3-pyridinylmethoxy)-2-naphthylsulfonyl)-4-azahomoadamantane, 3-(4-(3-pyridinylmethoxy)-2-naphthylsulfonyl)-3-azabicyclo[3.2.2]nonane, 3-(1-acetoxy-3-naphthylsulfonyl)-3-azabicyclo[3.2.2] nonane, 3-(1-hydroxy-3-naphthylsulfonyl)-3-azabicyclo[3.2.2] nonane, 3-[1-[1-(3-dimethylamino)-3-naphthylsulfonyl]]-3-azabicyclo[3.2.2]nonane, 4-(1-hydroxy-3-naphthylsulfonyl-(1-azahomoadamantane, 4-(1-acetoxy-3-naphthylsulfonyl)-4-azahomoadamantane, 4-(4-methoxy-1-naphthylsulfonyl)-4-azahomoadamantane, 3-(4-methoxy-1-naphthylsulfonyl)-3-azabicyclo[3.2.2] nonane, 3-(4-chloro-1-naphthylsulfonyl)-3-azabicyclo[3.2.2] nonane, 3-(1,2,3,4-tetrahydro-6-quinolinesulfonyl)-3-azabicyclo [3.2.2]nonane, 3-(5-acetoxy-2-naphthylsulfonyl)-3-azabicyclo[3.2.2] nonane, 6-(5-chloro-2-naphthylsulfonyl)-6-amino-1-hydroxy-2-azahomoadamantane, 4-(6-quinolinesulfonyl)-4-azahomoadamantane, 1-(6-quinolinesulfonyl)-1-azahomoadamantane, 3-(6-quinolinesulfonyl)-3-azabicyclo[3.2.2]nonane, 3-(5-chloro-2-naphthylsulfonyl)-3-aminonoradamantane, 2-(5-chloro-2-naphthylsulfonyl)-2-aminoadamantane, 2-(5-chloro-2-naphthylsulfonyl)-2-(3-aminopropyl)-2-aminoadamantane, 1-(5-chloro-2-naphthylsulfonyl)-1-phenyl-1,3-diaminopropane, 1-(2-naphthylsulfonyl)-1-aminoadamantane, 3-(5-chloro-2-naphthylsulfonyl)-3-azabicyclo[3.2.1] octane, 5-(5-chloro-2-naphthylsulfonyl)-2-thia-5-azabicyclo [2.2.1]heptane, 3-(2-naphthylsulfonyl)-3-azabicyclo[3.2.2]nonane, 4-(2-naphthylsulfonyl)-4-azahomoadamantane, 3-(1-methoxy-4-naphthylsulfonyl)-3-azabicyclo[3.2.2] nonane, 3-(5-amino-2-naphthylsulfonyl)-3-azabicyclo[3.2.2] nonane, or said pharmaceutically acceptable salt thereof.

19. A pharmaceutical composition, comprising:
(1) a pharmaceutically effective amount of a sulfonamide Compound according to claim 1; and
(2) a pharmaceutically acceptable carrier or diluent therefor.

20. The pharmaceutical composition of claim 19, wherein Q is a carbon atom and W is a nitrogen atom.

21. The pharmaceutical composition of claim 19, wherein Q is a nitrogen atom and W is a carbon atom.

22. The pharmaceutical composition of claim 19, wherein Q and W are each carbon atoms.

23. The pharmaceutical composition of claim 19, wherein Q and W are each carbon atoms, X is a chlorine atom, Y is a hydrogen atom, $R^1$ is an adamantyl group and $R^2$ is a hydrogen atom.

24. The pharmaceutical composition of claim 19, wherein Q and W are each carbon atoms, X is a chlorine atom, Y is a hydrogen atom, and $R^1$ and $R^2$ and the nitrogen atom to which they are mutually bonded form a bridged polycyclic moiety selected from the group consisting of 4-azahomoadamantane and 3-azabicyclo[3.2.2]nonane.

25. The pharmaceutical composition of claim 19, wherein Q and W are each carbon atoms, X is a hydrogen atom, Y is a 3-pyridinylmethoxy group, and $R^1$ and $R^2$ and the nitrogen atom to which they are mutually bonded form a bridged polycyclic moiety selected from the group consisting of 4-azahomoadamantane and 3-azabicyclo[3.2.2]nonane.

26. The pharmaceutical composition of claim 19, wherein said compound is a 5-Chloro-2-naphthalenesulfonamide derivative encompassed by formula (I).

27. The pharmaceutical composition of claim 19, wherein said compound of formula (I) is N-(1-adamantyl)-5-chloro-2-naphthalenesulfonamide, 4-(5-chloro-2-naphthylsulfonyl)-4-azahomoadamantane, 3-(5-chloro-2-naphthylsulfonyl)-3-azabicyclo[3.2.2]nonane, 4-[4-(3-pyridinylmethoxy)-2-naphnhylsulfonyl)-4-azahomoadamantane, 3-(4-(3-pyridinylmethoxy)-2-naphthylsulfonyl)-3-azabicyclo[3.2.2]nonane, 3-(1-acetoxy-3-naphthylsulfonyl)-3-azabicyclo[3.2.2]nonane, 3-(1-hydroxy-3-naphthylsulfonyl)-3-azabicyclo[3.2.2]nonane, 3-[1-[1-(3-dimethylamino)-3-naphthylsulfonyl]]-3-azabicyclo[3.2.2]nonane, 4-(1-hydroxy-3-naphthylsulfonyl)-4-azahomoadamantane, 4-(1-acetoxy-3-naphthylsulfonyl)-4-azahomoadamantane, 4-(4-methoxy-1-naphthylsulfonyl)-4-azahomoadamantane, 3-(4-methoxy-1-naphthylsulfonyl)-3-azabicyclo[3.2.2]nonane, 3-(4-chloro-1-naphthylsulfonyl)-3-azabicyclo[3.2.2]nonane, 3-(1,2,3,4-tetrahydro-6-quinolinesulfonyl)-3-azabicyclo[3.2.2]nonane, 3-(5-acetoxy-2-naphthylsulfonyl)-3-azabicyclo[3.2.2]nonane, 6-(5-chloro-2-naphthylsulfonyl)-6-amino-1-hydroxy-2-azahomoadamantane, 4-(6-quinolinesulfonyl)-4-azahomoadamantane, 1-(6-quinolinesulfonyl)-1-azahomoadamantane, 3-(6-quinolinesulfonyl)-3-azabicyclo[3.2.2]nonane, 3-(5-chloro-2-naphthylsulfonyl)-3-aminonoradamantane, 2-(5-chloro-2-naphthylsulfonyl)-2-aminoadamantane, 2-(5-chloro-2-naphthylsulfonyl)-2-(3-aminopropyl)-2-aminoadamantane, 1-(5-chloro-2-naphthylsulfonyl)-1-phenyl-1,3-diaminopropane, 1-(2-naphthylsulfonyl)-1-aminoadamantane, 3-(5-chloro-2-naphthylsulfonyl)-3-azabicyclo[3.2.1]octane, 5-(5-chloro-2-naphthylsulfonyl)-2-thia-5-azabicyclo[2.2.1]heptane, 3-(2-naphthylsulfonyl)-3-azabicyclo[3.2.2]nonane, 4-(2-naphthylsulfonyl)-4-azahomoadamantane, 3-(1-methoxy-4-naphthylsulfonyl)-3-azabicyclo[3.2.2]nonane, 3-(5-amino-2-naphthylsulfonyl)-3-azabicyclo[3.2.2]nonane, or said pharmaceutically acceptable salt thereof.

* * * * *